(12) United States Patent
Dalvi et al.

(10) Patent No.: US 11,986,289 B2
(45) Date of Patent: May 21, 2024

(54) ASSEMBLY FOR MEDICAL MONITORING DEVICE WITH MULTIPLE PHYSIOLOGICAL SENSORS

(71) Applicant: Willow Laboratories, Inc., Irvine, CA (US)

(72) Inventors: Cristiano Dalvi, Lake Forest, CA (US); Hung The Vo, Fountain Valley, CA (US); Jeroen Poeze, Rancho Santa Margarita, CA (US); Ferdyan Lesmana, Irvine, CA (US); Jesse Chen, Foothill Ranch, CA (US); Kevin Hughes Pauley, Lake Forest, CA (US); Ruiqi Long, Irvine, CA (US); Stephen Leonard Monfre, Lawrenceville, NJ (US); Sean Merritt, Lake Forest, CA (US); Mohamed K. Diab, Ladera Ranch, CA (US); Massi Joe E. Kiani, Laguna Niguel, CA (US)

(73) Assignee: Willow Laboratories, Inc., Irvine, CA (US)

( * ) Notice: Subject to any disclaimer, the term of this patent is extended or adjusted under 35 U.S.C. 154(b) by 688 days.

(21) Appl. No.: 16/697,814

(22) Filed: Nov. 27, 2019

(65) Prior Publication Data

US 2020/0163597 A1 May 28, 2020

Related U.S. Application Data

(60) Provisional application No. 62/771,818, filed on Nov. 27, 2018.

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0066* (2013.01); *A61B 5/0075* (2013.01);
(Continued)

(58) Field of Classification Search
CPC .............. A61B 5/14532; A61B 5/0066; A61B 5/02055; A61B 5/0075; A61B 5/01;
(Continued)

(56) References Cited

U.S. PATENT DOCUMENTS

| 4,960,128 A | 10/1990 | Gordon et al. |
| 4,964,408 A | 10/1990 | Hink et al. |

(Continued)

FOREIGN PATENT DOCUMENTS

| EP | 3 056 141 | 8/2016 |
| WO | WO 2019/014629 | 1/2019 |

OTHER PUBLICATIONS

US 2022/0192529 A1, 06/2022, Al-Ali et al. (withdrawn)
International Search Report and Written Opinion received in PCT Application No. PCT/US2018/042148, dated Nov. 19, 2018.

*Primary Examiner* — Devin B Henson
*Assistant Examiner* — Matthew Eric Ogles
(74) *Attorney, Agent, or Firm* — Knobbe, Martens, Olson & Bear, LLP

(57) ABSTRACT

Systems, methods, and apparatuses for enabling a plurality of non-invasive, physiological sensors to obtain physiological measurements from the same tissue site. Each of a plurality of sensors can be integrated with or attached to a multi-sensor apparatus. The multi-sensor apparatus can orient the plurality of non-invasive, physiological sensors such that each of the plurality of non-invasive, physiological sensors obtains physiological data from the same or a similar location.

20 Claims, 13 Drawing Sheets

(51) Int. Cl.
*A61B 5/01* (2006.01)
*A61B 5/0531* (2021.01)
(52) U.S. Cl.
CPC .............. *A61B 5/01* (2013.01); *A61B 5/0531* (2013.01); *A61B 2560/0462* (2013.01)
(58) Field of Classification Search
CPC ..... A61B 5/0462; A61B 5/0531; A61B 5/053; A61B 5/02416
See application file for complete search history.

(56) References Cited

U.S. PATENT DOCUMENTS

| | | | |
|---|---|---|---|
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| 5,436,499 A | 7/1995 | Namavar et al. | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,671,914 A | 9/1997 | Kalkhoran et al. | |
| 5,685,299 A | 11/1997 | Diab et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,987,343 A | 11/1999 | Kinast | |
| 5,995,855 A | 11/1999 | Kiani et al. | |
| 5,997,343 A | 12/1999 | Mills et al. | |
| 6,002,952 A | 12/1999 | Diab et al. | |
| 6,010,937 A | 1/2000 | Karam et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,040,578 A | 3/2000 | Malin et al. | |
| 6,045,509 A | 4/2000 | Caro et al. | |
| 6,066,204 A | 5/2000 | Haven | |
| 6,067,462 A | 5/2000 | Diab et al. | |
| 6,070,093 A * | 5/2000 | Oosta .................... A61B 5/1455 600/316 |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,115,673 A | 9/2000 | Malin et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,255,708 B1 | 7/2001 | Sudharsanan et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,280,381 B1 | 8/2001 | Malin et al. | |
| 6,285,896 B1 | 9/2001 | Tobler et al. | |
| 6,301,493 B1 | 10/2001 | Marro et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,411,373 B1 | 6/2002 | Garside et al. | |
| 6,415,167 B1 | 7/2002 | Blank et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,487,429 B2 | 11/2002 | Hockersmith et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,534,012 B1 | 3/2003 | Hazen et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,587,196 B1 | 7/2003 | Stippick et al. | |
| 6,587,199 B1 | 7/2003 | Luu | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,635,559 B2 | 10/2003 | Greenwald et al. | |
| 6,639,668 B1 | 10/2003 | Trepagnier | |
| 6,640,116 B2 | 10/2003 | Diab | |
| 6,640,117 B2 | 10/2003 | Makarewicz et al. | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kiani et al. | |

(56) References Cited

U.S. PATENT DOCUMENTS

| | | |
|---|---|---|
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,868,285 B2 * | 3/2005 | Muller-Dethlefs .......... A61B 5/14532 600/316 |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Ai-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Ai-Ai |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,430 B2 * | 8/2007 | Cho .................. A61B 5/14532 600/326 |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Ai-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |

(56) References Cited

U.S. PATENT DOCUMENTS

| | | |
|---|---|---|
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Ai-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |

(56) References Cited

U.S. PATENT DOCUMENTS

| | | |
|---|---|---|
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |

(56) References Cited

U.S. PATENT DOCUMENTS

| | | |
|---|---|---|
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Ai-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,759,714 B2 | 9/2017 | Bordelon et al. |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |

(56) References Cited

U.S. PATENT DOCUMENTS

| | | |
|---|---|---|
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,835,130 B2 * | 11/2020 | Cho .................. A61B 10/0064 |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| 10,959,651 B1 * | 3/2021 | McKinney ........... A61B 5/0075 |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1* | 7/2003 | Cohen ................ A61B 5/14532 |
| | | 600/316 |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2006/0211926 A1 | 9/2006 | Yu et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |

(56) References Cited

U.S. PATENT DOCUMENTS

| | | |
|---|---|---|
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0188538 A1 | 7/2012 | Patil et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0090537 A1 | 4/2013 | Schemmann et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0057530 A1* | 2/2015 | Roggeveen ........ A61B 17/3401 600/424 |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0354015 A1 | 12/2016 | Zhang et al. |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014056 A1* | 1/2017 | Newberry ............ A61B 5/1455 |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0100064 A1 | 4/2017 | Van Dorpe et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188864 A1 | 7/2017 | Drury |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224220 A1* | 8/2017 | Tunnell ..................... G01J 3/02 |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |

(56) References Cited

U.S. PATENT DOCUMENTS

| | | |
|---|---|---|
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0042513 A1* | 2/2018 | Connor .................. A61B 5/369 |
| 2018/0042557 A1* | 2/2018 | Park ...................... A61B 5/7221 |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0078155 A1 | 3/2018 | Baek et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Ai-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Ai-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0325722 A1 | 10/2019 | Kiani et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |

(56) References Cited

U.S. PATENT DOCUMENTS

| | | |
|---|---|---|
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |

\* cited by examiner

ASSEMBLY FOR MEDICAL MONITORING DEVICE WITH MULTIPLE PHYSIOLOGICAL SENSORS

CROSS-REFERENCE TO RELATED APPLICATIONS

The present application claims priority benefit to U.S. Provisional Application No. 62/771,818, entitled "Assembly For Medical Monitoring Device For Harmonizing Physiological Measurements," filed Nov. 28, 2018, which is hereby incorporated herein by reference in its entirety.

TECHNICAL FIELD

The present disclosure relates to physiological monitoring. More specifically, this disclosure relates to systems, methods, and apparatuses for measuring physiological parameters from overlapping or proximate regions of tissue using a plurality of non-invasive physiological sensors.

BACKGROUND

Monitoring of blood glucose (blood sugar) concentration levels has long been critical to the treatment of diabetes in humans. Current blood glucose monitors involve a chemical reaction between blood serum and a test strip, requiring an invasive extraction of blood via a lancet or pinprick. Small handheld monitors have been developed to enable a patient to perform this procedure anywhere, at any time. But the inconvenience of this procedure—specifically the blood extraction and the use and disposition of test strips—has led to a low level of compliance. Such low compliance can lead to serious medical complications. While a non-invasive method of measuring glucose has long been sought, attempts to create such a device have universally failed due to the difficult nature of detecting small concentrations of glucose in the blood.

SUMMARY

The present disclosure describes example systems, methods, and apparatuses for enabling a plurality of non-invasive, physiological sensors to obtain physiological measurements from the same tissue site. Each of a plurality of sensors can be integrated with or attached to a multi-sensor apparatus and can be oriented such that each sensor obtains physiological data from the same or a similar location.

In some cases, a multi-sensor apparatus includes a plurality of non-invasive sensors and a sensor head. The plurality of non-invasive sensors can be configured to obtain physiological data associated with a patient. The sensor head can include a frame and a tissue interaction section. The frame can be configured to support some or all of the plurality of non-invasive sensors. The tissue interaction section can be configured to be positioned proximate a tissue site of the patient. Each of the plurality of non-invasive sensors can be configured to obtain physiological data associated with a patient at the tissue site.

The multi-sensor apparatus of any of the preceding paragraphs and/or any of the multi-sensor apparatuses disclosed herein may include any combination of the following features described in this paragraph, among other features described herein. The tissue interaction section can include a different sensing region for each of the plurality of non-invasive sensors. A particular non-invasive sensor can obtain the physiological data via the particular sensing region. A distance between each of the sensing regions can satisfy a distance threshold. At least two of the plurality of noninvasive sensors can be configured to simultaneously obtain the physiological data. At least two of the plurality of noninvasive sensors can be configured to obtain the physiological data at non-overlapping time intervals. Each of the plurality non-invasive physiological sensors can obtain physiological data from of the same tissue site. The plurality non-invasive physiological sensors can obtain the physiological data from a plurality of regions of the tissue site. Each of the plurality of regions of the tissue site can be proximate to one of the plurality of regions of the tissue site.

The multi-sensor apparatus of any of the preceding paragraphs and/or any of the multi-sensor apparatuses disclosed herein may include any combination of the following features described in this paragraph, among other features described herein. The plurality of non-invasive sensors can include at least two of an optical coherence tomography (OCT) device, a Raman spectroscopy device, a near infrared (NIR) spectroscopy device, a bio-impedance-sensing device, a temperature-sensing device, or a pulse oximetry device. The plurality of non-invasive sensors can include an OCT device, a Raman spectroscopy device, a NIR spectroscopy device, a bio-impedance-sensing device, a temperature-sensing device, and/or a pulse oximetry device. The plurality of non-invasive sensors can include a Raman spectroscopy device, wherein the apparatus further comprises a Raman lens tube coupled to the sensor head. The tissue interaction region can be configured to contact the tissue site of the patient. The multi-sensor apparatus can include a processor. The processor can be configured to receive the physiological data from each of the plurality of noninvasive sensors; and determine a physiological parameter based at least in part on the physiological data. The physiological parameter can include a concentration of blood glucose.

In some cases, a system for measuring physiological parameters from a tissue site of a patient can include a multi-sensor apparatus and a processor. The multi-sensor apparatus can include a plurality of non-invasive sensors and a sensor head. The plurality of non-invasive sensors can be to obtain physiological data associated with a patient. The sensor head can include a frame and a tissue interaction section. The frame can be configured to support each of the plurality of non-invasive sensors. The tissue interaction section can be configured to be positioned proximate a tissue site of the patient. Each of the plurality of non-invasive sensors are configured to obtain physiological data from a same tissue site. The processor can be configured to receive the physiological data from each of the plurality of noninvasive sensors; and determine a physiological parameter based at least in part on the physiological data.

The system of any of the preceding paragraphs and/or any of the systems disclosed herein may include any combination of the following features described in this paragraph, among other features described herein. The tissue interaction section can include a plurality of sensing regions. Each of the plurality of sensing regions can correspond to one or more of the plurality of non-invasive sensors. A particular non-invasive sensor can obtain the physiological data via the particular sensing region. At least two of the plurality of noninvasive sensors can be configured to simultaneously obtain the physiological data. At least two of the plurality of noninvasive sensors can be configured to obtain the physiological data at non-overlapping time intervals. The plurality of non-invasive sensors can include at least two of an optical coherence tomography (OCT) device, a Raman spectroscopy device, a NIR spectroscopy device, a bio-impedance-sensing device, a temperature-sensing device, or a pulse oximetry device. The plurality of non-invasive sensors can include an OCT device, a Raman spectroscopy device, a NIR spectroscopy device, a bio-impedance-sensing device, a temperature-sensing device, and/or a pulse oximetry device. The physiological parameter can include a concentration of blood glucose.

The present disclosure describes example systems, methods, apparatuses, and medical devices for enabling a plurality of non-invasive, physiological sensors to obtain physiological measurements from the same or proximate regions of tissue of a patient. A multi-sensor apparatus can include a plurality of non-invasive, physiological sensors. The sensors can be integrated into or otherwise attached to multi-sensor apparatus and can be oriented and/or positioned on or within the multi-sensor apparatus such that each sensor is directed towards, or otherwise can obtain a measurement from, the same or a proximate measurement location corresponding to tissue of a patient.

The multi-sensor apparatus of any of the preceding paragraphs and/or any of the multi-sensor apparatuses disclosed herein may include any combination of the following features described in this paragraph, among other features described herein. The multi-sensor apparatus can include a frame configured to support at least a portion of each of the plurality of noninvasive sensors and can further include a sensor head having a surface for interacting with a tissue of the patient. The sensors can be oriented and/or positioned on or within the frame such that each of the sensors can obtain the physiological measurements from essentially the same, overlapping, or proximate regions of tissue of a patient. As a non-limiting example, in use, the sensor head can be placed in contact with patient's skin, and the sensors can obtain physiological measurements from tissue associated with the contact area, which can include an area defined by a perimeter of the surface of the sensor head. By enabling each of the plurality of sensors to obtain measurements from the overlapping or proximate tissue regions of tissue, the multi-sensor apparatus can advantageously facilitate the collection and/or correlation of sensor data received from the plurality of sensors. Furthermore, the multi-sensor apparatus can enable a determination, or a more accurate estimate, of one or more physiological parameters, such as those physiological parameters that are not readily determinable from sensor data from a single physiological sensor.

The multi-sensor apparatus of any of the preceding paragraphs and/or any of the multi-sensor apparatuses disclosed herein may include any combination of the following features described in this paragraph, among other features described herein. An example multi-sensor apparatus can include two or more of an optical coherence tomography (OCT) device, a Raman spectroscopy device, a NIR spectroscopy device, a bio-impedance-sensing device, a temperature-sensing device, a tissue dielectric constant sensor, or a pulse oximetry device. The sensors can be oriented or positioned such that they can obtain physiological data from overlapping, intersecting, touching, or proximate measurement sites. A processor can combine, collect and/or correlating at least some of the physiological data from the various sensors to improve or confirm measurements or to determine or estimate a physiological parameter. For example, a processor can determine or estimate a blood glucose concentration.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

BRIEF DESCRIPTION OF THE DRAWINGS

The following drawings and the associated descriptions are provided to illustrate embodiments of the present disclosure and do not limit the scope of the claims.

Figure 1:
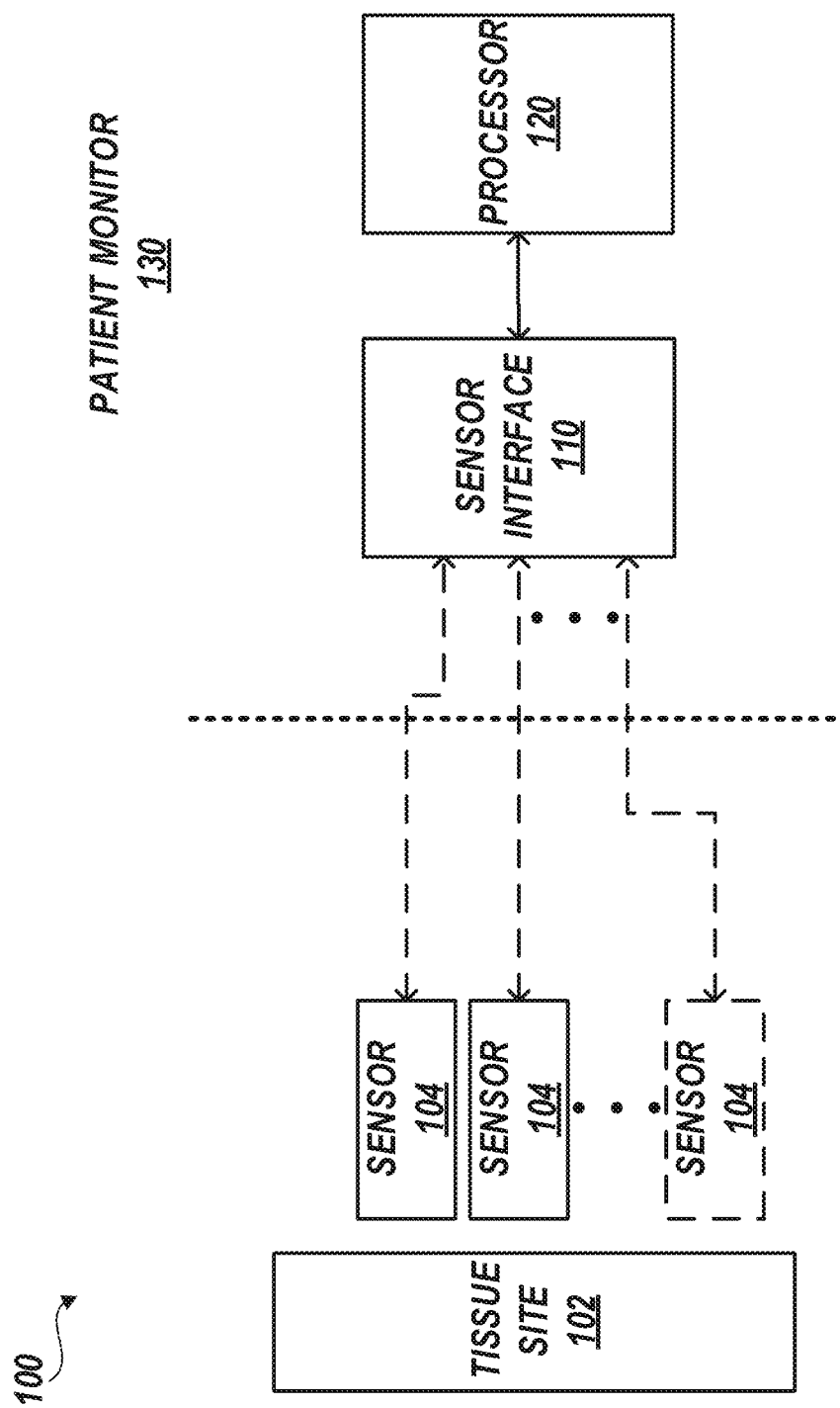
FIG. 1 is a block diagram illustrating an example patient monitoring system.

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

The present disclosure will now be described with reference to the accompanying figures, wherein like numerals refer to like elements throughout. The following description is merely illustrative in nature and is in no way intended to limit the disclosure, its application, or uses. It should be understood that steps within a method may be executed in different order without altering the principles of the present disclosure. Furthermore, examples disclosed herein can include several novel features, no single one of which is solely responsible for its desirable attributes or which is essential to practicing the systems, devices, and methods disclosed herein.

Overview

Many non-invasive techniques for determining blood glucose have significant shortcomings, such as low accuracy (for example, less accuracy than invasive home monitors) and insufficient specificity of glucose concentration measurement. Accordingly, there is a need for an improved method to non-invasively monitor glucose. Systems and methods disclosed herein address various challenges related to non-invasively determining a patient's blood glucose level by combing and/or correlating data from multiple non-invasive sensors. Each of the non-invasive sensors can interrogate the same or a similar tissue site of a patient. In this way, physiological parameters or other variables identified using one or more sensors can be utilized to improve data from one or more other sensors. Using these data collecting and/or combining techniques, a glucose concentration measurement can be obtained.

In many instances, a single non-invasive sensor may lack the functionality to obtain sufficient physiological information for an accurate determination of an analyte concentration, such as a glucose concentration measurement. As a result, many physiological monitoring techniques include estimations, such as those based on common assumptions, to compensate for the lack of known data. However, due to the sensitivity of analyte measurements, these estimations can result in inaccurate or unreliable determinations.

For example, Beer's Law (also known as the Beer-Lambert Law) relates the attenuation of light to properties of a material. In particular, Beer's law states that absorbance of a material is proportional to the concentrations of the attenuating species in the material sample. The relationship between these parameters is expressed in Equation 1 below:

$$A = \varepsilon * b * c \qquad \text{(Equation 1)}$$

where A is the absorbance of the material at a given wavelength of light, S is the molar absorptivity or extinction coefficient (L mol-1 cm-1), unique to each molecule and varying with wavelength, b is the length of the light path through the material (cm), and c is the concentration of an analyte of interest (mol L-1).

In many cases, the length of the light path through the material (sometimes referred to as the path length) is estimated. For example, a generic finger may be associated with a first estimated path length value, while a generic nose may be associated with a second path length value. However, every person has a unique tissue geometry, which can include, but is not limited to, unique skin structure or skin thickness. Furthermore, because tissue is not uniform throughout a person's body, even tissue sites that are close in proximity, such as two different measurements sites on a patient's finger, can have a different tissue geometry and/or optical profiles.

As noted above, a specific tissue geometry of a particular tissue site can affect the path length value, among other physiological parameters or variables. To this end, multiple noninvasive sensors can be configured to obtain physiological parameters from the same tissue site. It can be difficult for a caregiver to manually position multiple sensors to obtain data from the same tissue site. Thus, in some cases, a system or apparatus can include a frame or housing that supports each of the plurality of non-invasive sensors and orients the non-invasive sensors to obtain physiological data associated with the same tissue site. In some cases, two tissue sites are considered the same tissue site if one or more portions of the tissue sites overlap and/or one or more portions of the tissue sites are within a threshold distance of each other.

As another example, a non-invasive physiological sensor can be configured to obtain skin geometry data, which can be utilized to calculate a path length associated with a tissue site. In some such cases, the skin geometry data can be utilized to calibrate one or more sensors (for example, select a focal depth of a Raman spectrometer), which can result in more accurate analyte measurements, such as a blood glucose concentration measurement.

To aid in the correlation of data between the sensors, it can be desirable for each of the sensors to obtain data relating to the same tissue site. However, it can be difficult to position different sensors on the same tissue site without anything more than the caregiver's visual assessments. Similarly, it can be difficult to re-position the same sensor on the same tissue site after it has been removed from the patient. To solve these and other problems, tissue geometry information can be utilized to determine whether successive measurements have occurred in the same or a different location. Furthermore, in some cases, tissue geometry information can be utilized to guide the placement of one or more sensors to a particular tissue site.

An optical coherence tomography, or OCT, sensor can be utilized to obtain tissue geometry information. OCT is an optical imaging technique using light waves that produce high-resolution imagery of biological tissue. OCT creates its images by interferometrically scanning in depth a linear succession of spots, and measuring backscattered light at different depths in each successive spot. The OCT data can be processed to present an image of the linear cross section. OCT data can be processed to determine tissue geometry information, such as skin geometry. For example, the OCT data can provide data regarding a thickness of one or more skin layers, such as the epidermis, the dermo-epidermal junction, or the dermis.

In some cases, OCT data can be utilized to determine whether successive OCT measurements have occurred in the same or a different location (e.g., the same or a different tissue site). For example, each tissue site can relate to a specific optical profile and a particular tissue site can retain its specific optical profile over time. Furthermore, the specific optical profile of a particular tissue site can be different from the specific optical profile of some or all other tissue sites. In some cases, OCT data can be utilized to determine whether multiple OCT measurements have occurred in the same or a different location. In some cases, OCT data can be utilized to determine whether multiple non-OCT measurements have occurred in the same or a different location. For example, the position and/or orientation of an OCT sensor can be registered with the position and/or orientation of one or more other sensors, and successive OCT measurements can be utilized to determine whether a sensor has been placed in the same (or a different) location as a previously placed sensor.

A bio-impedance or tissue dielectric constant sensor can be utilized to obtain tissue geometry information. For example, bio-impedance or tissue dielectric constant data can provide information relating to one or more skin layers, a hydration of one or more skin layers, or a cellular structure of the tissue. In some cases, similar to as described above with respect to OCT data, bio-impedance or tissue dielectric constant data can be utilized to determine whether successive measurements have occurred in the same or a different location.

Raman spectroscopy has exhibited promise with respect to blood glucose detection, due to its capability to gain information about the molecular constitution non-invasively. For example, features such as peaks of the Raman spectra are considered the Raman "fingerprints" of analytes such as glucose. Accordingly, using an isolated or semi-isolated Raman signal, the system can identify physiological data, such as information regarding a patient's blood glucose level.

For various reasons, it has been challenging to isolate a pure Raman signal from a signal obtained from a Raman spectrometer. For example, emission of fluorescence in tissue often overwhelms any signal collected from the Raman spectrometer, thereby hiding Raman features. In addition, attenuation of the signal due to absorption can further affect prediction of analytes using the collected signal. Furthermore, varying tissue geometries at tissue sites increases the difficulty in selecting a focal depth of the Raman spectrometer that will optimize a resolution of the Raman signal. Systems, devices, and methods herein can include variety of noninvasive physiological sensors, such as any of those described in greater detail in International Pat. App. No. PCT/US2018/042148, filed Jul. 13, 2018, entitled "Medical Monitoring Device For Harmonizing Physiological Measurements," which is hereby incorporated herein by reference in its entirety.

Systems and methods disclosed herein can address one or more of these or other challenges by providing a multi-sensor apparatus that can utilize multiple sensors to obtain physiological data from the same tissue site. For example, the present disclosure addresses various challenges related to positioning and/or orienting multiple sensors to obtain physiological data from the same tissue site. In some instances, physiological data associated with the same tissue site can facilitate calibration or harmonization between sensors, or improve the accuracy of one or more other sensors.

Patient Monitoring System

FIG. 1 illustrates a block diagram of an example patient monitoring system 100. The patient monitoring system 100 includes a patient monitor 130 and a plurality of sensors (individually or collectively referred to as sensor 104 or sensors 104). The patient monitor 130 can include a sensor interface 110 and a processor 120. In some cases, each of the sensors 104 can obtain physiological measurements relating to the same tissue site 102. It will be understood that the patient monitoring system 100 can include fewer or more components as desired. For example, the patient monitoring system 100 can include fewer or more sensors 104 than illustrated in FIG. 1.

The plurality of sensors 104 can each be the same type of sensors, or one or more of the sensors 104 can be of a different type. For example, the plurality of sensors 104 can include, but are not limited to, an OCT sensor, a Raman spectrometry device, a pulse oximetry device, a bioimpedance sensor, a temperature sensor, an acoustic sensor, or a combination thereof.

As described herein, a particular tissue site can retain its specific optical profile over time, and that optical profile can be different from the optical profile of another tissue site. Accordingly, to aid in harmonizing data between the sensors 104, it can be advantageous for the sensors 104 to interrogate the same tissue site. Accordingly, two or more of the sensors 104 can be configured to obtain physiological measurements from the same tissue site 102. In some cases, two tissue sites can be considered the same tissue site if one or more portions of the tissue sites overlap with one another. In some cases, two tissue sites can be considered the same tissue site if one or more portions of the tissue sites touch or connect. In some cases, two tissue sites can be considered the same tissue site if one or more portions of the respective tissue sites satisfy a distance threshold. The distance threshold can vary across embodiments. For example, in some cases, a distance threshold can be satisfied if a first tissue site (e.g., corresponding to a first sensor) is less than 4, 8, 12, or 16 mm (+/−a few mm) from a second tissue site (e.g., corresponding to a second sensor). As another example, the distance threshold can be satisfied if the distance between two tissue sites is less than or equal to 30, 50, 70, or 90 mm. the distance threshold can be satisfied if the distance between two tissue sites is less than or equal to 1, 2.5, or 4 cm. In some cases, For example, two tissue sites can be considered the same tissue site if they include the same region of the patient's body (e.g., the same finger, thumb, thenar space, hand, wrist, forearm, nose, limb, head, ear, neck, upper body, or lower body). In some cases, one or more of the sensors 104 can be configured to obtain physiological measurements from the different tissue sites.

In some cases, one or more of the sensors 104 can be integrated into or coupled to an apparatus. In some cases, the apparatus, such as apparatus 200 of FIG. 2, is wearable by a user. For example, the apparatus can include a glove that when worn by a user allows the sensor 104 to interrogate the tissue site 102. As another example, the apparatus can include a sock, a shirt, a sleeve, a cuff, a bracelet, a headband, or the like. As described herein, in some cases, the apparatus includes a frame configured to support each of the sensors 104. The frame can orient the sensors 104 such that each of the sensors 104 can obtain physiological data associated with the same tissue site 102.

The patient monitor 130 can be configured to communicate (non-limiting example: via sensor interface 110) with one or more of the plurality of sensors 104 to receive sensor data, control the sensors 104, or the like. The sensor data can be utilized by the patient monitor 130 (non-limiting example: the processor 120) to determine one or more physiological parameters, patient vitals, or concentrations of one or more analytes associated with a patient. For example, based at least in part on sensor data from one or more of the sensors 104, the patient monitor 130 can determine an amount of light absorbed, transmitted through, or reflected at a tissue site, path length (for example, a distance that light travels through the tissue), concentration of an analyte, bioimpedance, tissue dielectric constant, pulse rate (PR), pulse pressure variation (PPV), pleth variability index (PVI®), stroke volume (SV), stroke volume variation (SVV), peripheral capillary oxygen saturation ($SpO_2$), mean arterial pressure (MAP), central venous pressure (CVP), pulse pressure (PP), perfusion index (PI), total hemoglobin (SpHb®), carboxyhemoglobin (SpCO®), methemoglobin (SpMet®), oxygen content (SpOC®), or acoustic respiration rate (RRa®), among other parameters. In some aspects, the patient monitor 130 can derive or use one or more relationships (for instance, a set of linear equations) from two or more of the determined parameters. The patient monitor 130 can utilize the one or more relationships to determine the patient's blood glucose concentration, systemic vascular resistance (SVR), CO, or arterial blood pressure (BP), among other parameters.

In some cases, data from a single sensor 104 may not provide enough reliable information to determine certain physiological parameters. For example, a number of factors can affect an accuracy of sensor data including, but not limited to, patient movement, sensor placement, interference, the type of sensor being used, the expansion and contraction of the patient's vascular system, assumptions made during calculations, skin temperature, pressure, or the like. In addition or alternatively, the determination of some physiological parameters (for example, glucose concentration) may require more information than a single sensor can provide. To solve this or other problems, the patient monitor 130 (or one or more of the sensors) can harmonize or compare data from two or more sensors 104, which can allow for a determination of more accurate or reliable data, or can allow for a determination of one or more additional physiological parameters, such as blood glucose concentration.

The patient monitor 130 can wirelessly, or using wires, receive a signal from one or more of the plurality of sensors 104. The received signal may take various forms, such as a voltage, a current, or charge. An operational amplifier (op-amp) of the patient monitor 130 can increase the amplitude, as well as transform the signal, such as from a current to a voltage. An anti-aliasing filter (AAF) of the patient monitor 130 can then process of the output signal from the op-amp to restrict a bandwidth of the output signal from the op-amp to approximately or completely satisfy the sampling theorem over a band of interest. An analog-to-digital convertor (ADC) of the patient monitor 130 can convert the output signal from the AAF from analog to digital. The output signal from the ADC can then be sampled by a processor 120 of the patient monitor 130 at a relatively high speed. The result of the sampling can next be down-sampled before waveform analysis may be performed.

Multi-Sensor Apparatus

A multi-sensor apparatus can include a plurality of non-invasive physiological sensors and can position and/or orient the sensors such that each of the sensors can obtain measurements from the same tissue site (sometimes referred to as a measurement site). In this way, each of the sensors obtain measurements corresponding to tissue having the same or similar properties, such as the same or similar optical profile, the same or similar tissue geometry, the same or similar analyte concentration, or the like. Sensor data from one or more of the sensors can be combined, correlated, or utilized to improve, calibrate, or corroborate data and/or calculations from or related to another sensor. Sensor data from one or more sensors can be combined and/or harmonized to determine or estimate a physiological parameter, such as blood glucose concentration.

Figure 2A:
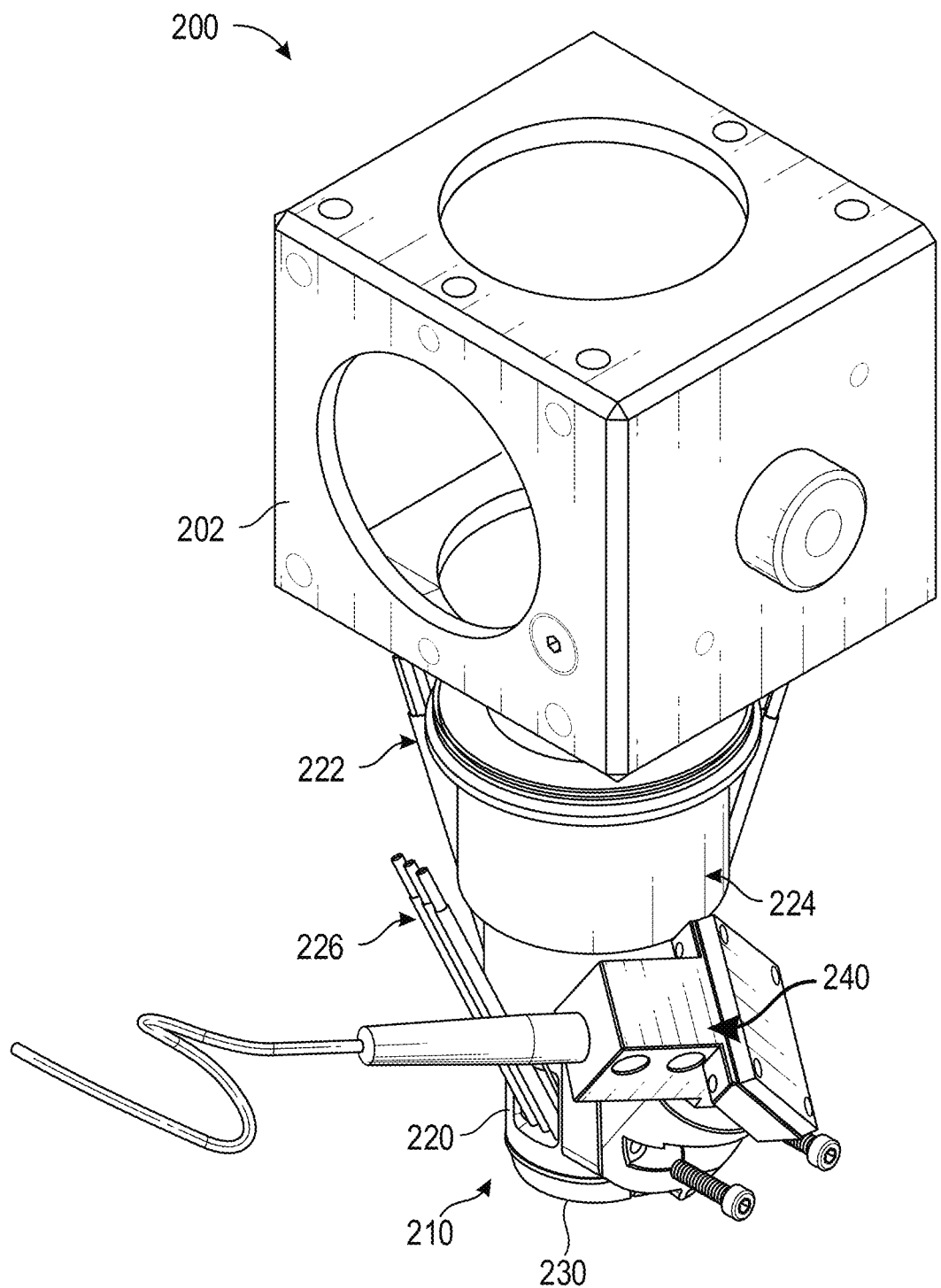
FIGS. 2A and 2B illustrate a perspective side views view of an example multi-sensor apparatus.
Figure 2B:
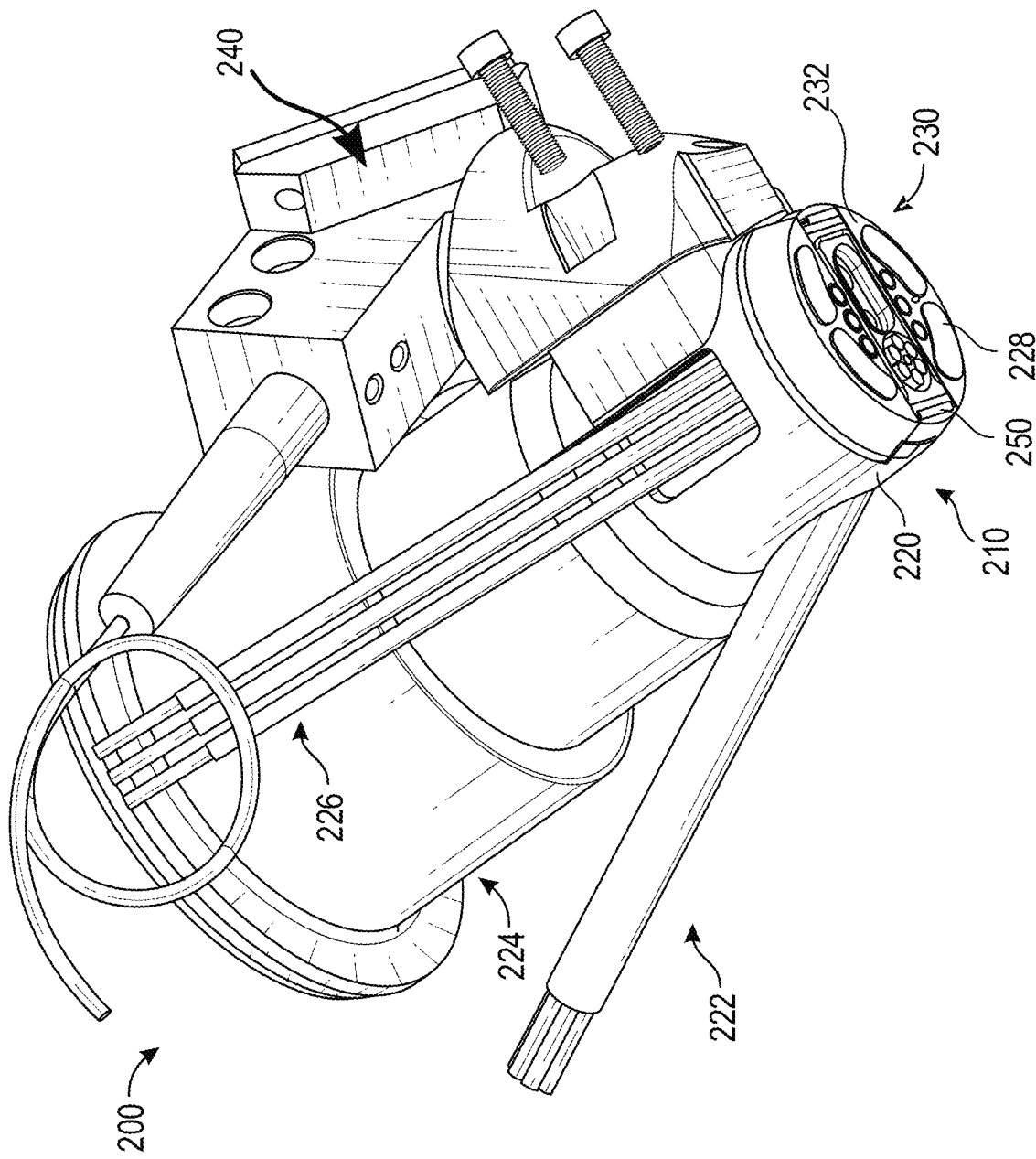

FIGS. 2A and 2B illustrate perspective side views of an example multi-sensor apparatus 200. As illustrated, the multi-sensor apparatus 200 includes a sensor head 210 (sometimes referred to as a fusion head), an optical mirror support 202, and fiber bundle 222, and fibers 226. Further, the multi-sensor apparatus 200 includes a plurality of sensors. In the example of FIGS. 2A and 2B, the plurality of sensors includes an OCT sensor 240, a Raman sensor 224, a bioimpedance sensor 228, and a temperature sensor 250 (collectively or individually referred to as sensor 104 or sensors 104). It will be understood that the multi-sensor apparatus 200 can include fewer, additional, or different components. For example, in some cases, the sensors 104 can include a tissue dielectric constant sensor, a NIR spectroscopy device, or a pulse oximetry sensor.

The sensor head 210 can include a frame 220 (sometimes referred to as a housing) and a tissue interaction section 230. The frame 220 can support one or more of sensors 104. For example, the frame 220 can be configured to receive, couple to, or integrate with one or more of the sensors 104. In some cases, the frame 220 includes or defines one or more cavities of a size and shape capable of accepting one or more of the sensors 104. In some cases, some or all of the sensors 104 are positioned and/or oriented on or within the frame 220 such that the sensors 104 are positioned and/or oriented on or within the frame 220 such that the sensors 104 are positioned and/or oriented on or within the frame 220 such that the sensors 104 can, in use, obtain measurements from the same, or essentially the same, tissue site. For example, as illustrated, each of the sensors 104 can be oriented within the frame 220 such that the sensors 104 point or are directed towards the tissue site 102.

The tissue interaction section 230 can include one or more openings through which the sensors 104 can emit light, receive lights, obtain measurements, etc. As described in more detail herein, the openings in the tissue interaction section 230 through which the sensors 104 emit light, receive lights, obtain measurements, etc. can be referred to a sensing region. The size, number, and location of the sensing regions in the tissue interaction section 230 can vary across embodiments. For instance, in the illustrated example of in FIG. 2B, the tissue interaction section 230 includes four sensing regions for the bioimpedance sensor 228, two sensing regions for the temperature sensor 250, a sensing region for the fiber bundle 222 (e.g., a pulse oximetry sensor), six sensing regions for the fiber 226, a sensing region for the OCT sensor 240, and a sensing region for the Ramen sensor 224. It will be understood that the position, number, size and/or shape of a sensing region can vary across embodiments. For example, a sensing region for the Raman sensor 224 can be large enough to include the spot size of an excitation source that may be part of the Raman sensor 224. Additionally or alternatively, a sensing region for the OCT sensor 240 can be large enough to allow for the excitation source of the OCT sensor 240 to scan the tissue site or to account for movement of the excitation source during use or manufacture.

The tissue interaction section 230 can be a centralized location at which the sensors 104 obtain measurements. In some such cases, the tissue interaction section 230 can encompass or include each of the sensing regions of the sensors 104. In this way, the sensors 104 can be oriented to obtain measurements from the same tissue site. In some cases, tissue sites can be considered the same tissue site if one or more portions of the tissue sites overlap with one another, if one or more portions of the tissue sites touch or connect, or if the tissue sites reside on the same region of the patient's body. As another example, in some cases, tissue sites can be considered the same tissue site if a distance between the tissue sites satisfies a distance threshold. For example, a distance threshold between sensing regions of two sensors can be satisfied if the sensing regions are less 4, 8, 12, or 16 mm (+/−a few mm) away from each other. As another example, the distance threshold between sensing regions of two sensors can be satisfied if the sensing regions are less than 30, 50, 70, or 90 mm (+/−a few mm) away from each other. As another example, the distance threshold between sensing regions of two sensors can be satisfied if the sensing regions are less than 1, 2.5, or 4 cm (+/−a few cm) away from each other.

The shape of the lower surface 232 of the tissue interaction section 230 can vary across embodiments. For example, in some cases, the lower surface 232 can be relatively flat. As another example, in some cases, the lower surface 232 can include one or more curvatures or concavities. A curvature of the lower surface 232 can be of a similar curvature to that of the area of the measured tissue site. As an example, the tissue site may be a finger nail and the curvature of the lower surface 232 can follow the approximate curvature of the finger nail. In some examples, the curvature of the lower surface 232 can match a specific curvature of the tissue site of the user. For example, the lower surface 232 can be molded, formed, or otherwise shaped according to a shape of the tissue site. In some cases, the curvature or shape of the lower surface 232 can be generic to the approximate curvature of a tissue site of the user. For example, the lower surface 232 can be molded, formed, or otherwise shaped according to the approximate curvature of an adult human finger nail where the tissue site is a finger nail.

The shape of the tissue interaction section 230 and/or the bottom of the sensor head 210 can vary across embodiments. For example, as illustrated in FIG. 2B, the tissue interaction section 230 and/or the bottom of the sensor head can be relatively circular. Alternatively, the tissue interaction section 230 and/or the bottom of the sensor head can be relatively square, rectangular, oval, elliptical, triangular, or the like.

The size of the tissue interaction section 230 can vary across embodiments. In some cases, the tissue interaction section 230 can have a length, width, and/or diameter on the scale of a few millimeters, decimeters, or centimeters. For example, the tissue interaction section 230 can have a length, width, and/or diameter of between 5 mm and 30 mm or between 10 mm and 20 mm, such as about 12.7 mm (+/−a few mm). As another example, the tissue interaction section 230 can have a length, width, and/or diameter of between 0.5 cm and 5 cm or between 1 cm and 3 cm.

In use, the tissue interaction section 230 can be placed on or positioned proximate to a tissue site. For example, in some cases, the tissue interaction section 230 can be configured to contact the tissue site. As another example, in some cases, the tissue interaction section 230 can be configured to hover over the tissue site such that a gap exists between at least a portion of the tissue interaction section 230 and the tissue site.

The tissue interaction section 230 can be attached to the tissue site of a patient using a permanent or temporary adhesive, by permanent or temporary implantation, via a wearable device, or other suitable means of temporarily, semi-permanently, or permanently securing a component to a tissue site. In some examples, the tissue interaction section 230 may be secured to a tissue site of a patient via a semi-permanent adhesive capable of securing the attachment component for a day or more. For example, the tissue interaction section 230 may be secured to a tissue site with a medical adhesive, glue, tape, or other means of adhering components to a tissue site.

The size and/or shape of the multi-sensor apparatus 200 can vary across embodiments. For example, in some implementations, the multi-sensor apparatus 200 can be sized to fit in the palm of a user's hand or is otherwise a handheld apparatus. In some cases, it can be desired for the multi-sensor apparatus 200, or at least the sensor head 210, to be relatively small such that the measurement site is also relatively small, such as less than 5, 10, 15, or 20 millimeters in diameter. However, the size of the measurement site can vary across embodiments and can be based on a number of factors, including, but not limited to, a number of sensors integrated into the multi-sensor apparatus 200.

In some cases, the multi-sensor apparatus 200 can be compatible with different sensor heads. For example, the different sensors heads can include various shapes and/or sizes, and a particular sensor head can be configured for use with a particular tissue site. That is, in some cases, a particular sensor head may be configured for use with a finger, while another sensor head may be configured for use with a toe, an ear, a forearm, or the like.

The sensor head 210 can be made of plastic or other lightweight material so as to reduce weight and/or cost. In some examples, the sensor head 210 can include brackets for securing components, such as sensors 104, to the frame 220.

In some implementations, the multi-sensor apparatus 200 can optionally include a battery (not shown). The battery can include various types of batteries, such as AA or AAA batteries. The battery can be configured to provide power to multi-sensor apparatus 200, such as to one or more of the sensors 104.

Figure 3A:
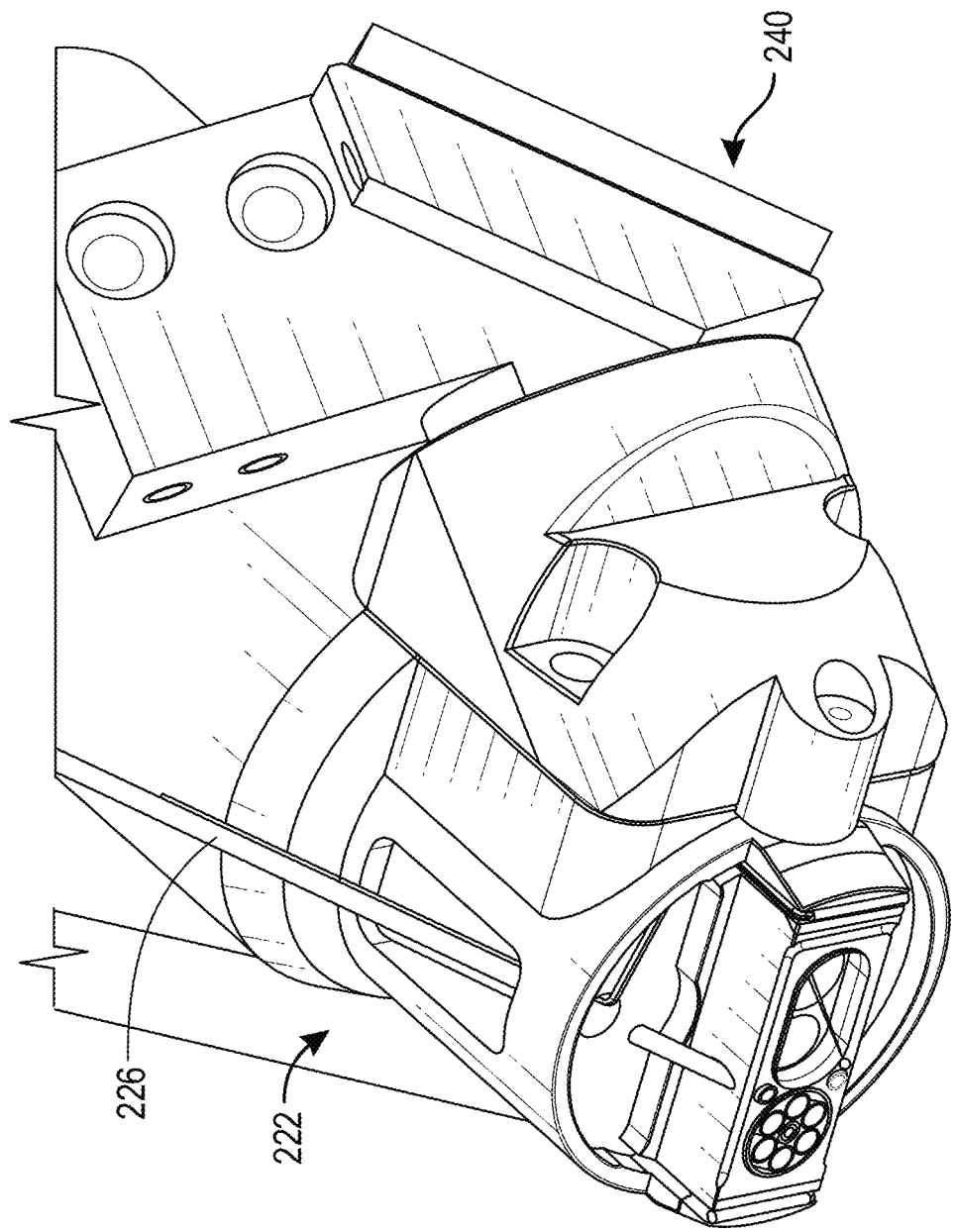
FIG. 3A illustrates a scaled perspective view of the multi-sensor apparatus of FIGS. 2A and 2B with portions of the sensor head removed.

FIG. 3A illustrates a scaled perspective view of the multi-sensor apparatus 200 of FIGS. 2A and 2B with portions of the sensor head 210 removed. Specifically, FIG. 3A illustrates the assembly of the bioimpedance sensors 228 removed from the multi-sensor apparatus 200 of FIGS. 2A and 2B, thereby showing various channels of the frame 220 through which the sensors 104 reside.

Figure 3B:
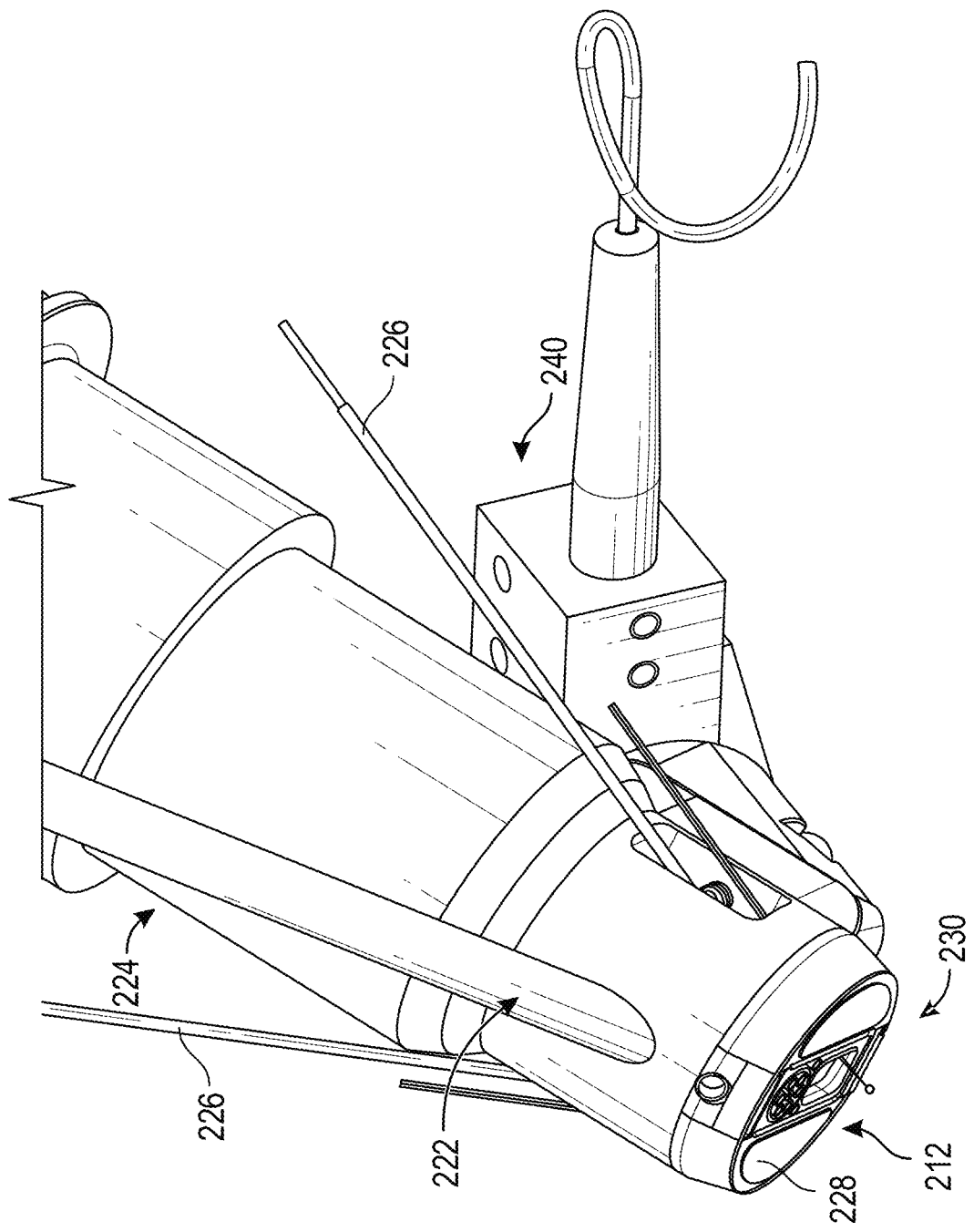
FIG. 3B illustrates scaled a perspective view of an example multi-sensor apparatus.

FIG. 3B illustrates scaled a perspective view of an example multi-sensor apparatus 200, which includes a different configuration of the tissue interaction section 230, as compared to FIGS. 2A and 2B. In the illustrated example of FIG. 3B, the tissue interaction section 230 includes two sensing regions for the bioimpedance sensor 228, a sensing region for the fiber bundle 222, a sensing region for the OCT sensor 240, and a sensing region for the Raman sensor 224. It will be understood that the position and number of openings corresponding to each sensor can vary across embodiments.

Assembly of a Multi-Sensor Apparatus

Figure 4A:
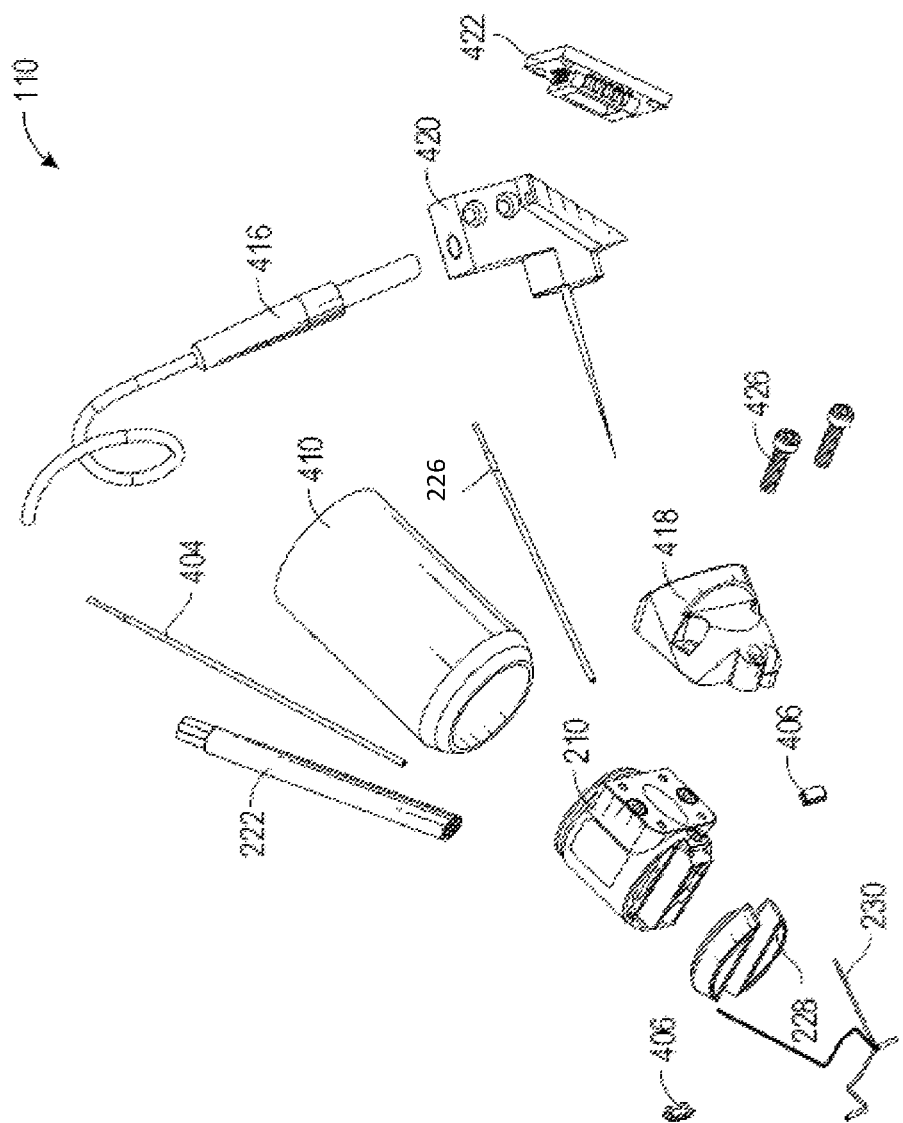
FIGS. 4A-4C are exploded view of various embodiments of a multi-sensor apparatus.
Figure 4B:
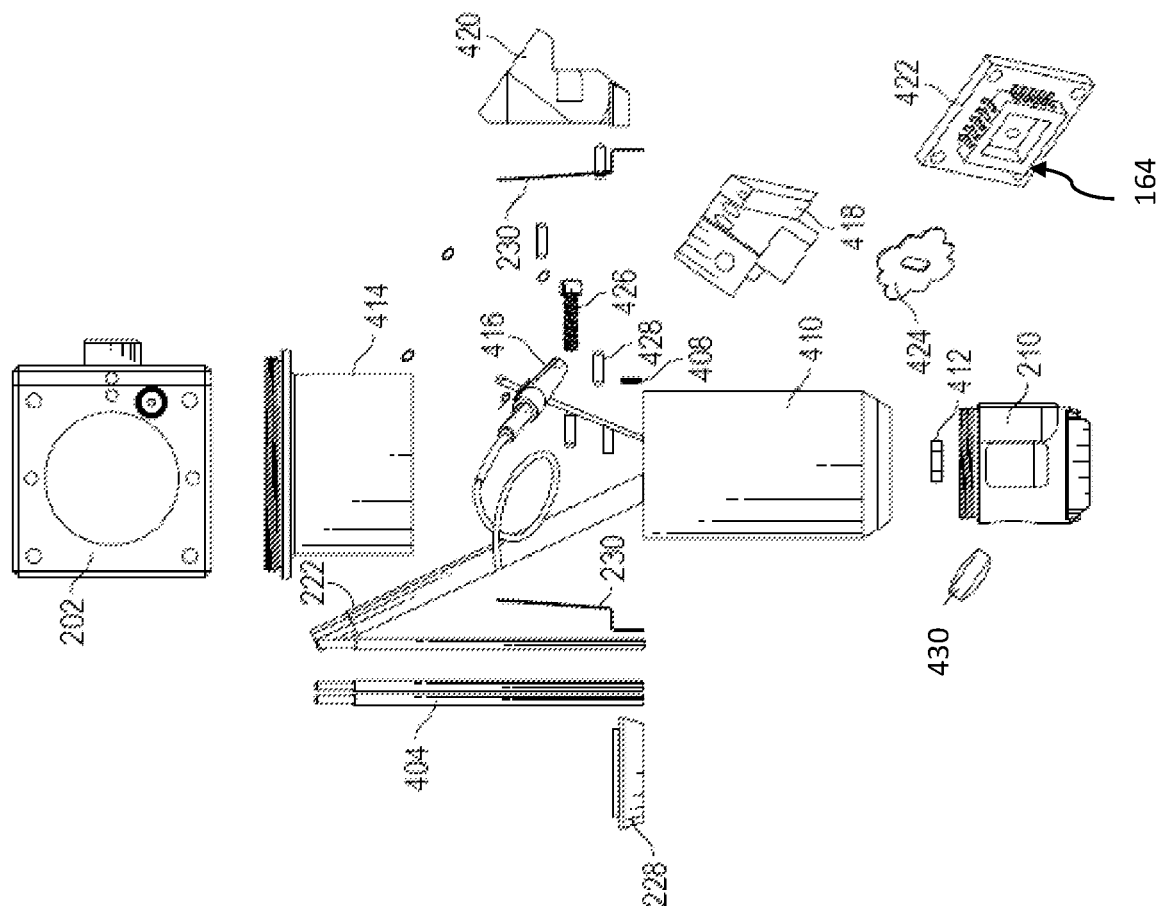
Figure 4C:
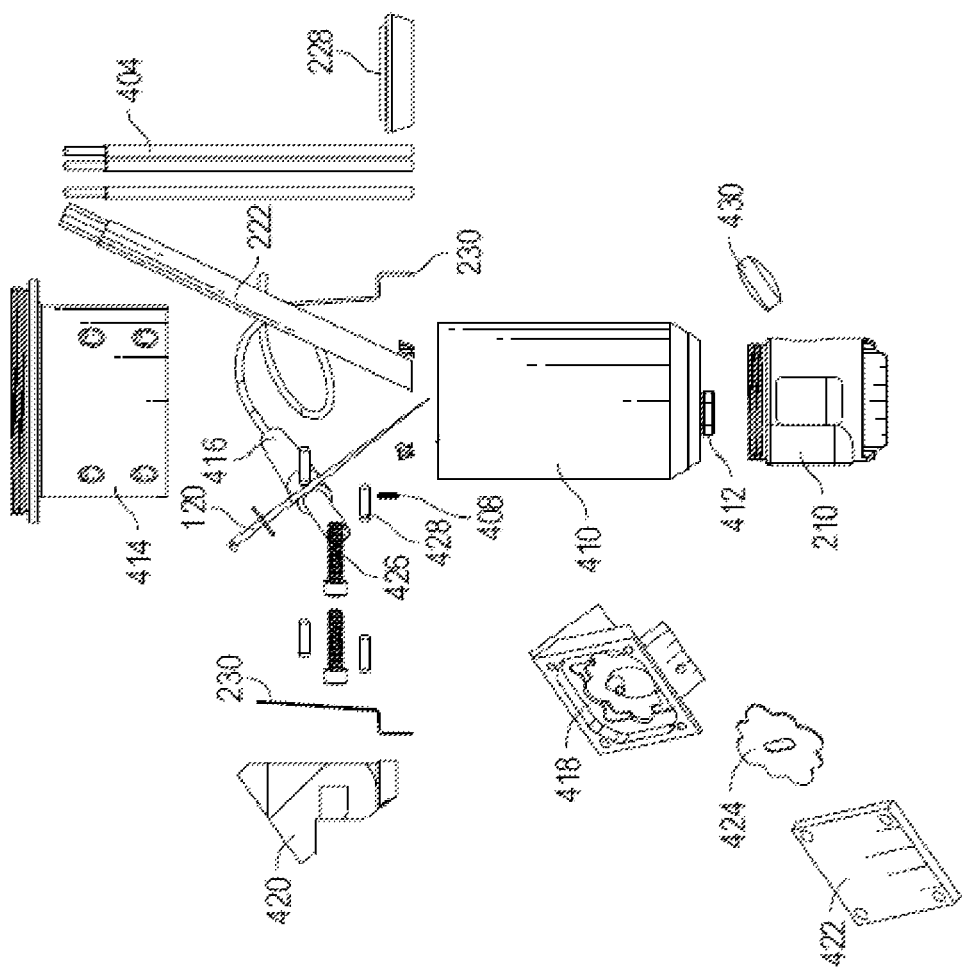

FIGS. 4A-4C are exploded views of an example multi-sensor apparatus 200. As shown, the multi-sensor apparatus 200 can include a pulse oximetry device (for example, including a fiber bundle 222 or multi-LED fibers 226), a temperature sensor 250 (for example, a thermistor), a temperature sensor support 406, a bioimpedance sensor 228, an O ring 408, a Raman sensing device 224, an OCT device 240, a sensor head 210, or any combination thereof. The Raman sensing device can include a Raman lens tube 410, a glass window 412, or a cube adaptor 414. The OCT device can include an OCT light source 416, a mirror block 418, an OCT coupler 420, a mirror 422, and/or a baffle 424. Further, the multi-sensor apparatus 200 can include one or more components to couple the components of the multi-sensor apparatus 200, such as one or more screws 426, bolts, or slotted spring pins 428, among other things. It will be understood that fewer, more, or different components can be used to implement the multi-sensor apparatus 200 or any of the sensors, as desired.

Pulse Oximetry Device

The multi-sensor apparatus 200 can include one or more components for pulse oximetry, such as one or more light sources for emitting light of one or more of a variety of wavelengths and one or more detectors for detecting the light after attenuation by tissue of a patient. The detected signal(s) can be communicated to a patient monitor 130, where the patient monitor 130 can remove noise, preprocesses the signal(s), and/or determine one or more physiological parameters associated with the patient.

In the illustrated example exploded views of the multi-sensor apparatus 200 of FIGS. 4A-4C, the components for pulse oximetry can include one or more multi-LED fibers 226 or a fiber bundle 222. For example, the one or more multi-LED fibers 226 or a fiber bundle 222 can include a light source and/or a detector. The light source can output one or more of a variety of wavelengths, including, but not limited to, near infrared (NIR), infrared (IR), or red wavelengths. The one or more detectors can detect the light after attenuation by tissue of a patient.

In some cases, the multi-LED fibers 226 or a fiber bundle 222 can be coupled to the sensor head 210. The sensor head 210 can orient or position the multi-LED fibers 226 or the fiber bundle 222. In use, the surface 212 of the sensor head 210 can be positioned on or proximate to a desired measurement site (for example, a portion of the patient's skin) and the multi-LED fibers 226 or the fiber bundle 222 can be utilized to obtain measurements from the measurement site on which the surface 212 is placed. It is understood that fewer, additional, or different light sources with fewer, additional, or different wavelengths can be utilized.

Optical Coherence Tomography (OCT)

The multi-sensor apparatus 200 can include one or more components for OCT. OCT is an optical imaging technique using light waves that produce high-resolution imagery of tissue. OCT creates its images by focusing a beam of light into a medium and interferometrically scanning the depth of a linear succession of spots and measuring the absorption and/or the scattering of the light at different depths in each successive spot. In some cases, the data can be processed to present an image of the linear cross section of the medium scanned.

In the illustrated example exploded views of the multi-sensor apparatus 200 of FIGS. 4A-4C, the components for OCT can include a light source 416 (non-limiting example: an optical fiber), an OCT scanner (e.g., a mirror block 418 and a mirror 422), an OCT coupler 420. In some cases, the mirror block 418 can couple to the light source 416, the mirror 422, and the OCT coupler 420. In addition, the OCT coupler 420 can couple to the sensor head 210 via one or more screws 426. Furthermore, the components for OCT can include a baffle 164 configured to fit within a portion of the mirror block and located between the light source 416 and the mirror 422, a lens 430 located between the mirror 422 and the sensor head 210, and/or a glass window 412 located within the sensor head 210. It will be noted, however, that the multi-sensor apparatus 200 can include fewer, additional, or different components for OCT. Additionally, the OCT device can be incorporated for Time Domain OCT or Fourier Domain OCT techniques. The choice among the OCT techniques can be defined, for example, by the specificity of the interested data.

The light source 416 can output a beam of light having a broad spectrum of wavelengths. In some cases, the beam of light can be collimated and pass a beam splitter such that a portion of the beam of light is directed towards the tissue and a portion of the beam of light is directed toward a reference arm, such as mirror 422. The light can be either polarized or non-polarized. In some cases, a polarizer located on one edge of a beam splitter can polarize the light linearly, elliptically, or circularly, as desired. As a non-limiting example, the wavelength can be centered at, for example, 1310 nm with a 50 nm bandwidth. In other cases, the wavelength can be centered at 1060 nm with a 70 nm bandwidth. Still, in other cases, the light source can be selected to have a center wavelength anywhere between 400 nm and 1700 nm with a bandwidth of up to 150 nm. It is understood that different light sources with different bandwidths can be chosen to optimize penetration depth into the tissue and optimize the depth resolution of sensitivity to skin structures.

The mirror 422 can be translated or moved to raster scan a depth image of the tissue. In some cases, the mirror 422 can be translated or moved to fine-tune OCT measurements. In addition or alternatively, an angle of the mirror 422, relative to one or more axes, can be adjusted. For example, multi-sensor apparatus 200 can be configured to move or shift the mirror 422, such as by means of a stepper motor, a piezo-electric actuator, or the like.

The reflected light from the tissue can be collected using a converging lens, such as lens 430 (FIG. 4C), and be directed to a photodetector where it can be recombined with a portion of a reference arm beam to form an interference pattern. OCT can provide a non-invasive method for identifying one or more characteristics of a tissue's structure or geometry. For example, a processor can use the signals from the photodetector to render a three dimensional image of the tissue.

Bioelectrical Impedance

The multi-sensor apparatus 200 can include one or more components for bioelectrical impedance. Bioelectrical impedance can be characterized as the principle that tissues and/or fluids of a patient have different impedances, that is, opposition to the flow of the electric current, which in turn may be dependent on variables such as water and electrolyte content, to name a few. Analysis of bioelectrical impedance can be performed to examine electrical, capacitive, or resistive characteristics of tissue to provide information on a noninvasive basis, such as tissue geometry.

As illustrated in the example exploded views of the multi-sensor apparatus 200 of FIGS. 4A-4C, the components for bioelectrical impedance can include two bioimpedance sensors 228 coupled to the sensor head 210. It will be noted, however, that the multi-sensor apparatus 200 can include fewer, additional, or different bioimpedance sensors 228. In use, the bioimpedance sensors 228 can apply an electrical signal to tissue, such as the tissue associated with the region defined by the perimeter of the sensor head 210.

Raman Spectroscopy

The multi-sensor apparatus 200 can include one or more components for Raman spectroscopy. As illustrated in the example exploded views of the multi-sensor apparatus 200 of FIGS. 4A-4C, the components for Raman spectroscopy can include a cube adaptor 414 and a Raman lens tube 410 and a dichroic mirror can be installed within the cube to guide the excitation and collection light beams 404. In addition, the Raman lens tube 410 can couple to (for example, screw together with) the sensor head 210. Furthermore, the components for Raman spectroscopy can include a Raman free space cone within the sensor head 210, a glass window 412, and/or a light source.

The components for Raman spectroscopy can include a light source. In some cases, the light source includes or produces a light, such as a laser beam. The characteristics of the light can vary across embodiments. For example, the light can have a tight bandwidth and/or stable spectrum. As another example, in some cases, the light can be centered between 600 nanometers and 900 nanometers, between 750 nanometers and 850 nanometers, centered at 785 nanometers, centered at 830 nanometers, or the like. Furthermore, the wavelength of the light can vary across embodiments. For example, in some cases, the light can have any wavelength(s) of a range of wavelengths varying from visible to NIR spectrum. In some cases, the light can be directed to the tissue by means of a dichroic mirror, focusing lens, and/or an optical window contacting the patient tissue. In some cases, the components for Raman spectroscopy are selected to avoid issues such as, but not limited to, reflections, fluorescence or scattering. In some cases, an optical window can be manufactured from quartz glass, coated with anti-reflecting material. It will be noted, however, that the multi-sensor apparatus 200 can include fewer, additional, or different components for Raman spectroscopy.

The Raman effect is a light-scattering phenomenon that can provide insight as to one or more characteristics of an analyte in a sample. When light irradiates a tissue, a fraction of the light is scattered, meaning it emerges in directions other than that of the incident (incoming) beam. Most of this scattered light (generally referred to as Rayleigh scattering) emerges at the original frequency ($f_0$) and wavelength of the incident beam. A small portion of the scattered light, however, emerges at some shifted frequency ($f_s$) that is different from, and usually lower than, the original frequency ($f_0$) and has wavelengths different from that of the incident light. Stokes shifted Raman can be at relatively longer wavelengths, and anti-stokes Raman can be at relatively shorter wavelengths. The process leading to this small portion of the scattered light is termed the Raman effect or Raman scattering.

Raman scattering can occur with a change in vibrational or rotational energy of a molecule. Accordingly, the Raman spectra can contain information about the specific chemical substance in the irradiated tissue. For example, Raman scattering yields a set of characteristic peaks in a spectrum, which is a "fingerprint" of a specific chemical substance. Raman spectroscopy has exhibited promise with respect to blood glucose detection, as well as the determination of other physiological data. Furthermore, Raman spectroscopy can by utilized with one or more other sensors to enhance or improve physiological data measurements or determinations. For example, data acquired from one or more sensors can be utilized to remove or reduce an effect of the fluorescence, or tissue absorption, refraction, scattering, and/or reflection.

Multi-Sensor Apparatus

As described herein, each of the sensors 104 of a multi-sensor apparatus 200 can be oriented or positioned to obtain measurements associated with a sensing region location with the perimeter of the sensor head 210.

Figure 5A:
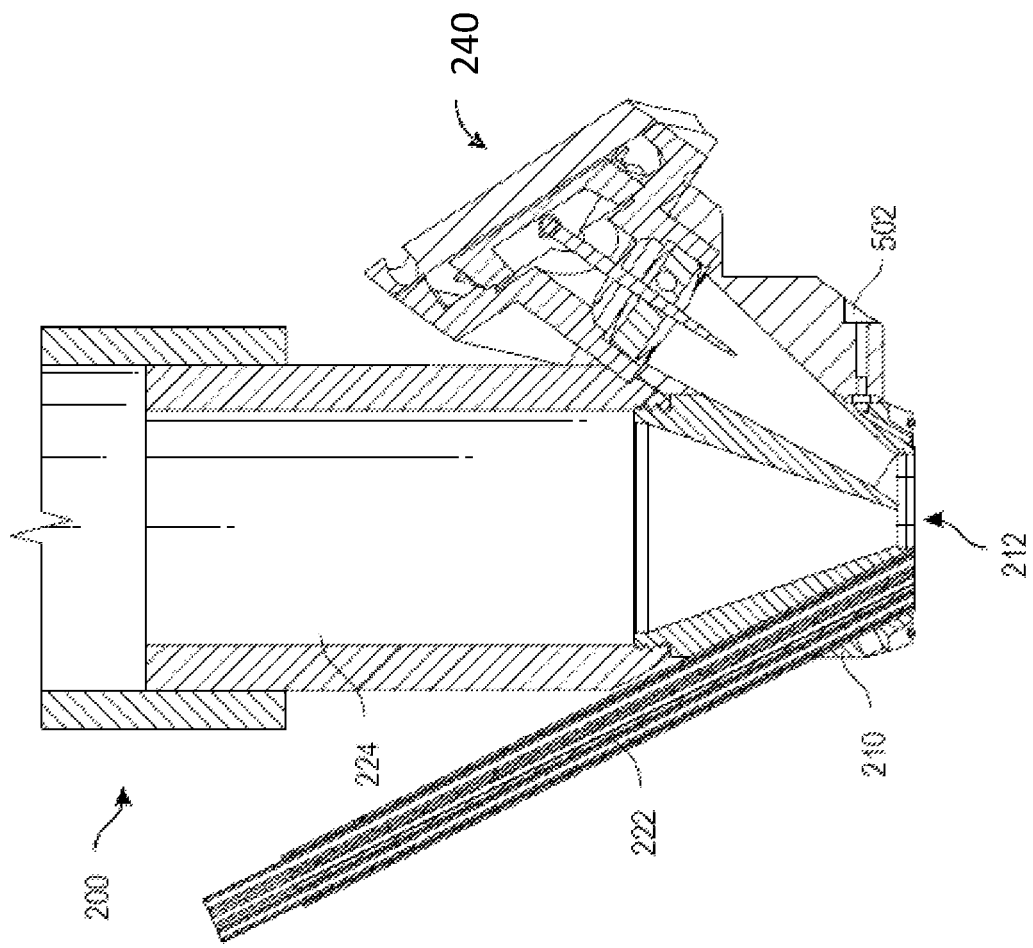
FIG. 5A is a cross-sectional view of an example multi-sensor apparatus.
Figure 5B:
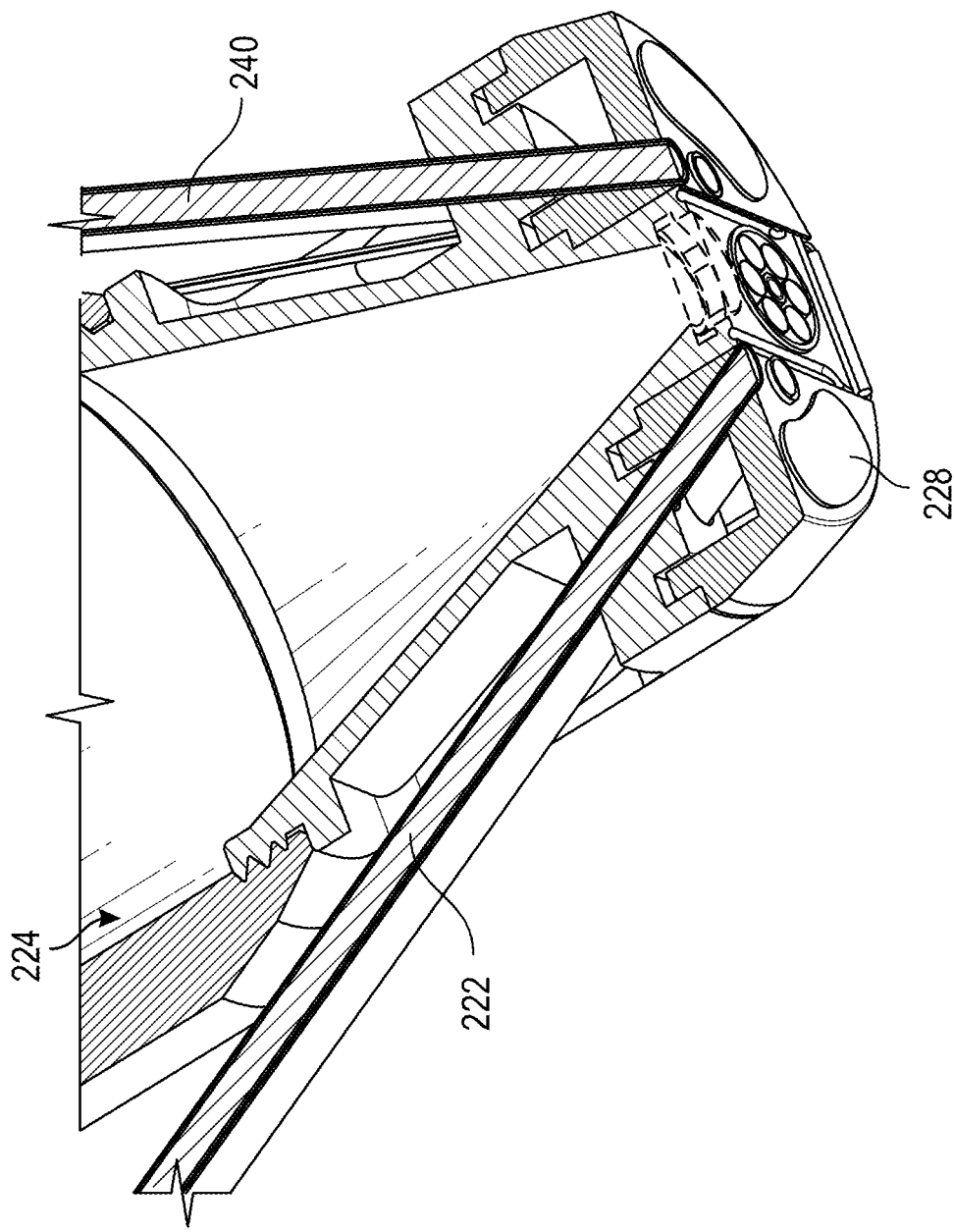
FIG. 5B illustrates a scaled cross-sectional view of an example multi-sensor apparatus.

FIG. 5A is a cross-sectional view of an example multi-sensor apparatus 200, and FIG. 5B illustrates a scaled cross-sectional view of an example multi-sensor apparatus 200, and provides an illustrative example of some of the cavities of the multi-sensor apparatus 200. As illustrated, the fiber bundle 222, Raman sensor 224, an OCT sensor 240, and a coupling agent port 622 are each oriented such that a sensing region of each the sensors is located within the region defined by the perimeter of the sensor head 210. That is, the frame of the multi-sensor apparatus 200 advantageously orients the sensors such that, in use, the sensors can obtain measurements from essentially the same, overlapping, or proximate regions of tissue. By orienting and/or positioning the sensors to interrogate or analyze essentially the same, overlapping, or proximate regions of tissue, the multi-sensor apparatus 200 can ensure that each of the sensors obtain measurements corresponding to tissue having the same or similar properties (non-limiting examples: the same or similar optical profile, the same or similar tissue geometry, the same or similar analyte concentration, or the like). As a result, in some cases, data from the one or more sensors can be utilized to improve, calibrate, or confirm data and/or calculations related to another sensor, thereby improving a determination or an accuracy of one or more physiological parameters. It will be understood that fewer, additional, or different sensors can be included in the multi-sensor apparatus 200.

Coupling Agent

Figure 5C:
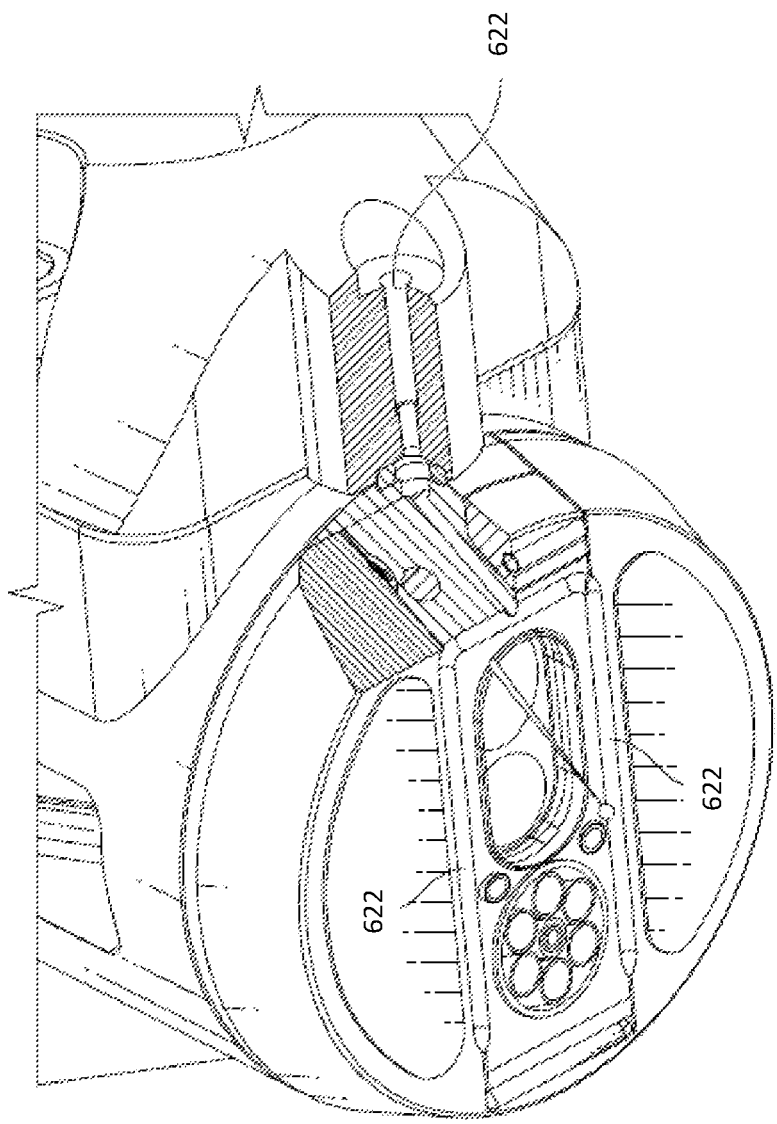
FIG. 5C illustrates a distribution channel of an example coupling agent of an example multi-sensor apparatus.

FIG. 5C illustrates a distribution channel of an example coupling agent port 622 of an example multi-sensor apparatus 200. In some cases, the multi-sensor apparatus 200 can be configured to apply a coupling agent to the tissue, for example, by introducing the coupling agent to the tissue via the coupling agent port 622. Among other things, a coupling agent can reduce variations in surface reflection of the sample tissue, thereby improving accuracy of the non-invasive measurement of the sample tissue. In addition, optical properties and/or temperature of the sample tissue can be stabilized by application of the coupling agent. By way of non-limiting example, the coupling agent can include a perfluorinated liquid. One such perfluorinated liquid is known by the brand name Fluorinert™ FC-70 or FC-40, manufactured by 3M Company, of St. Paul, Minnesota. In some embodiments the coupling agent can also be suppressed, for example if the optical properties of the tissue are acceptable.

Sensor Head

Figure 6A:
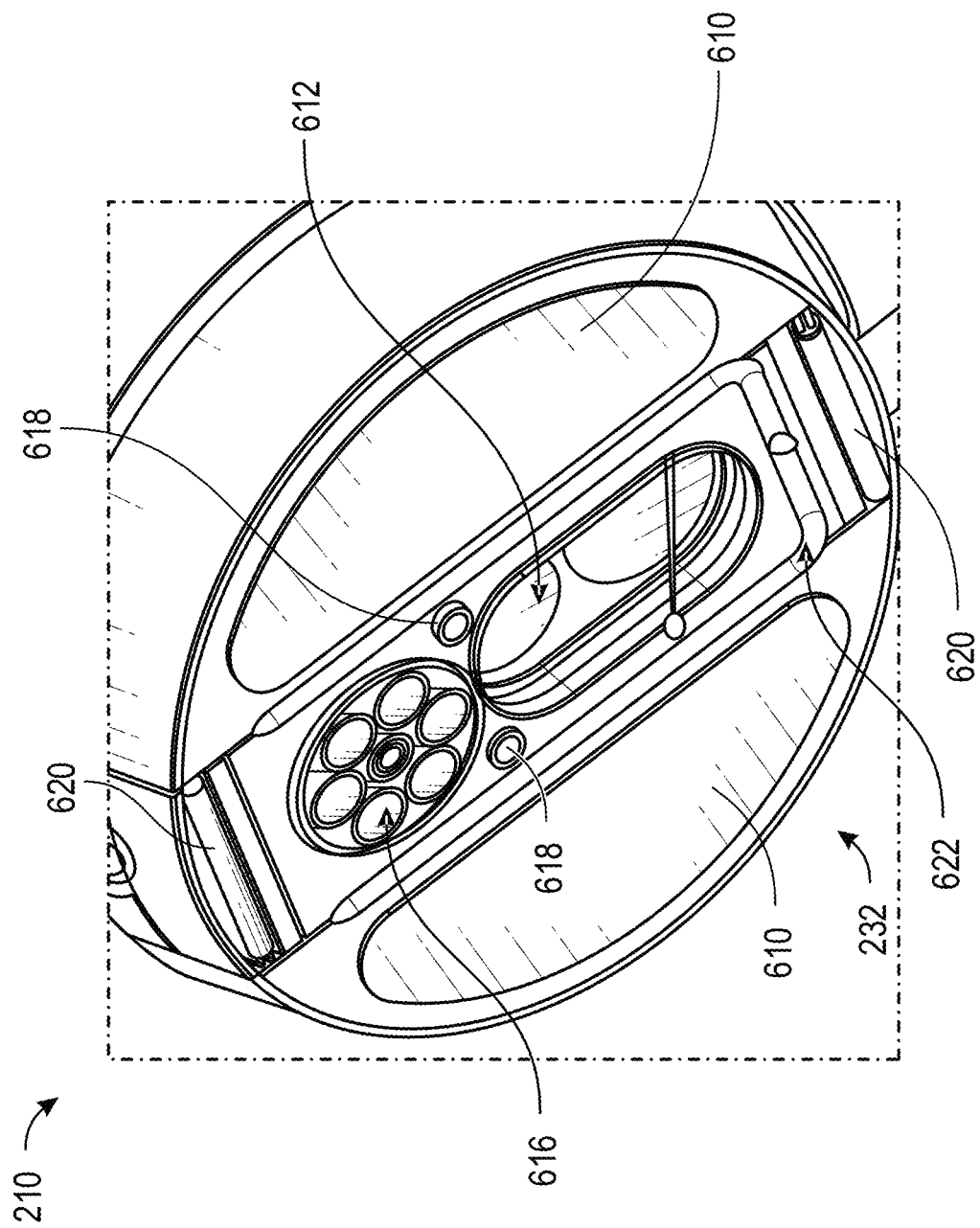
FIGS. 6A and 6B illustrate perspective and bottom views, respectively, of embodiments of a sensor head of a multi-sensor apparatus.
Figure 6B:
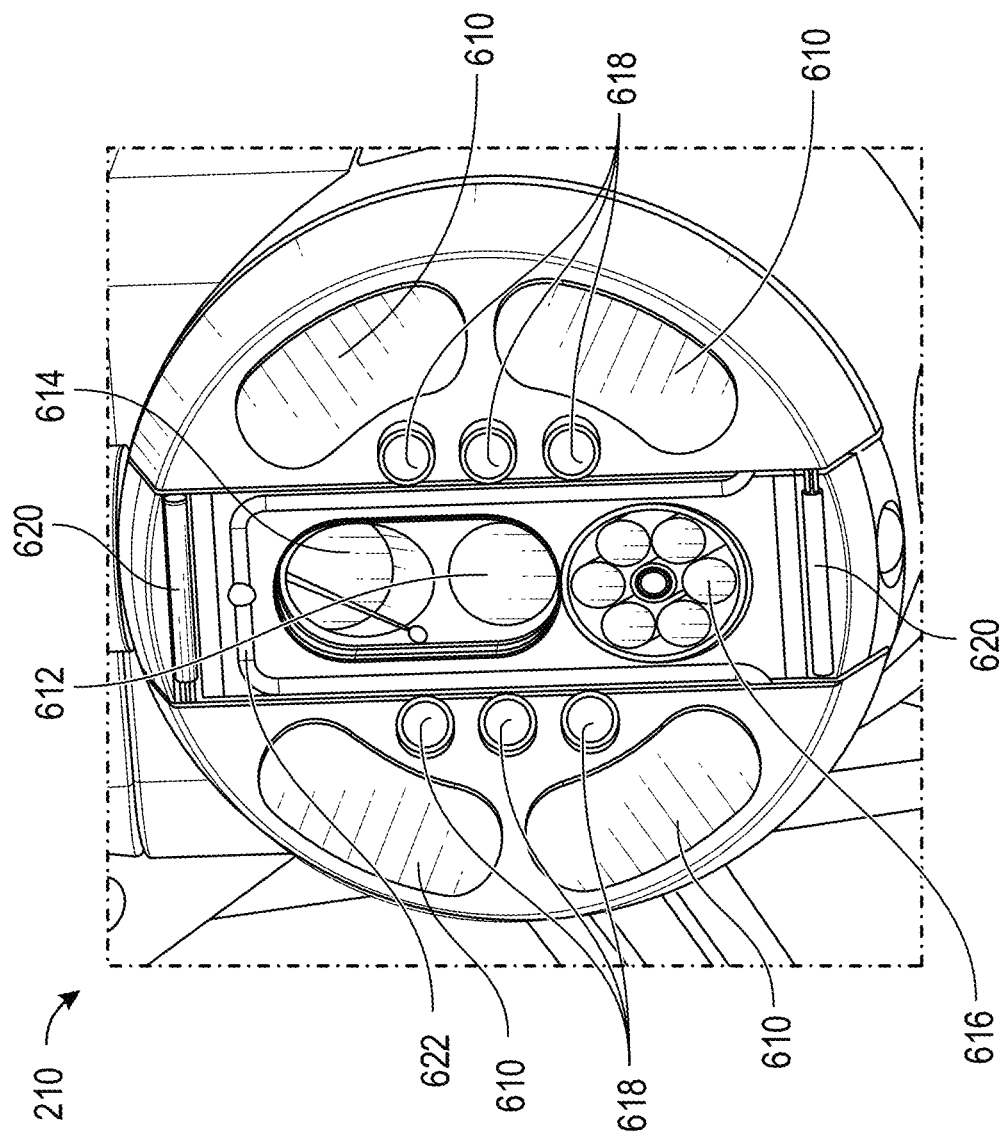

FIGS. 6A and 6B illustrate perspective and bottom views, respectively, of embodiments of a sensor head 210 of a multi-sensor apparatus 200. As described herein, each of the sensors of a multi-sensor apparatus 200 can include a sensing region on the sensor head 210 such that the sensors are each oriented or positioned to obtain measurements associated with the same tissue site.

The sensor head 210 can include a lower surface 232 for interacting with tissue of a patient. For example, in use, the lower surface 232 of the sensor head 210 can be positioned to contact or hover over the patient's skin. As illustrated in FIGS. 6A-6B, the lower surface 232 of the sensor head 210 can be relatively flat. Alternatively, the lower surface 232 of the sensor head 210 can include one or more contours. For example, the lower surface 232 of the sensor head 210 can be contoured or curved to align with a contour or curvature of the patient's tissue, such as the patient forearm, toe, or finger.

The sensor head 210 can be various shapes depending on the embodiment. For example, as illustrated in FIGS. 6A and 6B, the sensor head 210 can have a generally circular shape. In addition or alternatively, the sensor head 210 can have a generally square, rectangular, triangular, or elliptical shape or a combination thereof.

Portions of the lower surface 232 of the sensor head 210 can be partitioned into sensing areas of the plurality of non-invasive physiological sensors. For example, at least one of the sensing areas 610 can correspond to a sensing area for the bio-impedance sensors 228, a Raman sensing area 612 can correspond to a sensing area for a Raman sensor 224 of a Raman spectrometry device, an OCT sensing area 614 can correspond to a sensing area for an OCT sensor 240 of an OCT device, a fiber bundle sensing area 616 can correspond to a sensing area of fiber bundle 222, a multi-LED fiber sensing area 618 can correspond to a sensing area of multi-LED fibers 226, a temperature sensing area 620 can correspond to a sensing area of the temperature sensor 250, and/or a coupling agent sensing area 622 can correspond to coupling agent port 622.

The sensor head 210 and/or the lower surface 232 of the sensor head 210 can be sized to fit the sensing areas (non-limiting examples: sensing areas 610, 612, 614, 616, 618, 620, or 622) corresponding to each of the non-invasive physiological sensors. Accordingly, the size of the sensor head 210 can vary, for example, depending on the number of physiological sensors, the size or orientation of the sensing areas 610, 612, 614, 616, 618, 620, or 622, the distance between sensing areas 610, 612, 614, 616, 618, 620, or 622, or a combination thereof. In general, the sensor head 210 is sized such that each of the physiological sensors of the multi-sensor apparatus 200 can obtain measurements associated with essentially the same, overlapping, or proximate regions of tissue.

To aid in ensuring that the sensors obtain measurements associated with essentially the same, overlapping, or proximate regions of tissue, the sensor head 210 can have a length, width, and/or diameter on the scale of a few millimeters, decimeters, or centimeters. For example, the sensor head 210 can have a length, width, and/or diameter of between 5 mm and 30 mm or between 10 mm and 20 mm, such as about 12.7 mm (+/–a few mm). As another example, the sensor head 210 can have a length, width, and/or diameter of between 0.5 cm and 5 cm or between 1 cm and 3 cm.

Each of the sensing areas 610, 612, 614, 616, 618, 620, or 622 can have various shapes or sizes. As an example, the bio-impedance sensing areas 610 can each have a length, width, and/or diameter of between 5 mm and 30 mm (+/−a few mm) or between 10 mm and 20 mm (+/−a few mm). As another example, the Raman sensing area 612 can have a length, width, and/or diameter of between 1 mm and 10 mm (+/−a few mm) or between 2 mm and 4 mm (+/−a few mm), such as 2.25 mm. As another example, the OCT sensing area 614 can have a length, width, and/or diameter of between 1 mm and 10 mm (+/−a few mm) or between 2 mm and 4 mm (+/−a few mm), such as 2.5 mm. As another example, the sensing area 616 can have a length, width, and/or diameter of between 1 mm and 10 mm (+/−a few mm) or between 2 mm and 4 mm (+/−a few mm). As another example, the temperature sensing areas 620 can have a length, width, and/or diameter of between 1 mm and 5 mm (+/−a few mm) or between 3 mm and 4 mm (+/−a few mm). In some cases, the temperature sensing areas 620 are 3.5 mm by 0.4 mm (+/−a few 0.1 mm). As another example, the sensing areas 618 can have a length, width, and/or diameter of between 0.2 mm and 10 mm (+/−a few mm) or between 1 mm and 4 mm (+/−a few mm). As described above, the multi-LED fibers 226 can include one or more visible or NIR emitters and one or more detectors. In some cases, the emitters can be 1, 2, 3, 4, or 5 mm (+/−a few mm) from a detector. As another example, the coupling agent sensing areas 622 can have a length, width, and/or diameter of between 5 mm and 30 mm (+/−a few mm) or between 10 mm and 20 mm (+/−a few mm).

By enabling each of the plurality of sensors to obtain measurements from essentially the same, overlapping, or proximate regions of tissue, the multi-sensor apparatus 200 can advantageously facilitate the integration, correlation, and/or harmonization of sensor data received from the plurality of sensors. Furthermore, the multi-sensor apparatus 200 can enable a determination, or a more accurate estimate, of one or more physiological parameters, such as those physiological parameters that are not readily determinable from sensor data from a single physiological sensor.

EXAMPLES

Various example features can be found in the following clauses, which can be implemented together with any combination of the features described above:

Clause 1. A multi-sensor apparatus measuring physiological parameters from a tissue site of a patient, the apparatus comprising:
a plurality of non-invasive sensors configured to obtain physiological data associated with a patient; and
a sensor head comprising:
a frame configured to support each of the plurality of non-invasive sensors, and
a tissue interaction section configured to be proximate a tissue site of the patient, wherein each of the plurality of non-invasive sensors are configured to obtain physiological data associated with a patient at the tissue site.

Clause 2. The apparatus of Clause 1, wherein the tissue interaction section comprises a different sensing region for each of the plurality of non-invasive sensors, wherein a particular non-invasive sensor obtains the physiological data via the particular sensing region.

Clause 3. The apparatus of Clause 2, wherein a distance between each of the sensing regions satisfies a distance threshold.

Clause 4. The apparatus of any of the previous clauses, wherein at least two of the plurality of noninvasive sensors are configured to simultaneously obtain the physiological data.

Clause 5. The apparatus of any of the previous clauses, wherein at least two of the plurality of noninvasive sensors are configured to obtain the physiological data at non-overlapping time intervals.

Clause 6. The apparatus of any of the previous clauses, wherein each of the plurality non-invasive physiological sensors obtains physiological data from of the same tissue site.

Clause 7. The apparatus of any of the previous clauses, wherein the plurality non-invasive physiological sensors obtain the physiological data from a plurality of regions of the tissue site, wherein each of the plurality of regions of the tissue site is proximate to one of the plurality of regions of the tissue site.

Clause 8. The apparatus of any of the previous clauses, wherein the plurality of non-invasive sensors comprises at least two of an optical coherence tomography (OCT) device, a Raman spectroscopy device, a bio-impedance-sensing device, a temperature-sensing device, or a pulse oximetry device.

Clause 9. The apparatus of any of the previous clauses, wherein the plurality of non-invasive sensors comprises an OCT device, a Raman spectroscopy device, a bio-impedance-sensing device, a temperature-sensing device, and a pulse oximetry device.

Clause 10. The apparatus of any of the previous clauses, wherein the plurality of non-invasive sensors comprises a Raman spectroscopy device, wherein the apparatus further comprises a Raman lens tube coupled to the sensor head.

Clause 11. The apparatus of any of the previous clauses, wherein the tissue interaction region is configured to contact the tissue site of the patient.

Clause 12. The apparatus of any of the previous clauses, further comprising a processor configured to:
receive the physiological data from each of the plurality of noninvasive sensors; and
determine a physiological parameter based at least in part on the physiological data.

Clause 13. The apparatus of Clause 12, wherein the physiological parameter comprises a concentration of blood glucose.

Clause 14. A system for measuring physiological parameters from a tissue site of a patient, the system comprising:
a multi-sensor apparatus, the multi-sensor apparatus comprising:
a plurality of non-invasive sensors configured to obtain physiological data associated with a patient; and
a sensor head comprising:
a frame configured to support each of the plurality of non-invasive sensors, and
a tissue interaction section configured to be proximate a tissue site of the patient, wherein each of the plurality of non-invasive sensors are configured to obtain physiological data from a same tissue site; and
one or more processors in communication with the multi-sensor apparatus, the one or more processors configured to:
receive the physiological data from each of the plurality of noninvasive sensors; and
determine a physiological parameter based at least in part on the physiological data.

Clause 15. The system of Clause 14, wherein the tissue interaction section comprises a plurality of sensing regions, wherein each of the plurality of sensing regions corresponds to one or more of the plurality of non-invasive sensors, wherein a particular non-invasive sensor obtains the physiological data via the particular sensing region.

Clause 16. The system of any of Clauses 14 or 15, wherein at least two of the plurality of noninvasive sensors are configured to simultaneously obtain the physiological data.

Clause 17. The system of any of Clauses 14 to 16, wherein at least two of the plurality of noninvasive sensors are configured to obtain the physiological data at non-overlapping time intervals.

Clause 18. The system of any of Clauses 14 to 17, wherein the plurality of non-invasive sensors comprises at least two of an optical coherence tomography (OCT) device, a Raman spectroscopy device, a bio-impedance-sensing device, a temperature-sensing device, or a pulse oximetry device.

Clause 19. The system of any of Clauses 14 to 18, wherein the plurality of non-invasive sensors comprises an OCT device, a Raman spectroscopy device, a bio-impedance-sensing device, a temperature-sensing device, and a pulse oximetry device.

Clause 20. The system of any of Clauses 14 to 19, wherein the physiological parameter comprises a concentration of blood glucose.

Various example features can be found in the following clauses, which can be implemented together with any combination of the features described above:

Clause 1. An apparatus comprising:
a plurality of non-invasive sensors configured to obtain physiological data associated with a patient; and
a sensor head comprising:
a surface configured to contact a region of tissue of the patient, and
a frame configured to support at least a portion of each of the plurality of noninvasive sensors, wherein the plurality of noninvasive sensors are oriented and/or positioned on or within the frame such that each of the plurality of noninvasive sensors obtain the physiological data from tissue associated with the region of tissue in contact with the surface of the sensor head.

Clause 2. The apparatus of Clause 1, wherein the surface of the sensor head is less than 15 millimeters in diameter.

Clause 3. The apparatus of any of the previous clauses, wherein at least two of the plurality of noninvasive sensors are configured to simultaneously obtain the physiological data.

Clause 4. The apparatus of any of the previous clauses, wherein at least two of the
plurality of noninvasive sensors are configured to obtain the physiological data at non-overlapping time intervals.

Clause 5. The apparatus of any of the previous clauses, wherein the plurality of non-invasive sensors comprises at least two of an optical coherence tomography (OCT) device, a Raman spectroscopy device, a bio-impedance-sensing device, a temperature-sensing device, a NIR spectrometer device or a pulse oximetry device.

Clause 6. The apparatus of any of the previous clauses, wherein the plurality of non-invasive sensors comprises a Raman spectroscopy device, wherein the apparatus further comprises a Raman lens tube coupled to the sensor head.

Clause 7. The apparatus of Clause 6, wherein a sensing region of the Raman spectroscopy device is less than 3 millimeters in diameter.

Clause 8. The apparatus of Clause 6, wherein a sensing region of the Raman spectroscopy device is between 2 and 5 millimeters in diameter.

Clause 9. The apparatus of Clause 6, wherein a sensing region of the Raman spectroscopy device is between 3 and 15 millimeters in diameter.

Clause 10. The apparatus of Clause 6, wherein a sensing region of the Raman spectroscopy device is between 10 and 25 millimeters in diameter.

Clause 11. The apparatus of Clause 6, wherein a sensing region of the Raman spectroscopy device is greater than 15 millimeters in diameter.

Clause 12. The apparatus of any of the previous clauses, wherein the plurality of non-invasive sensors comprises a NIR spectroscopy device, wherein the apparatus further comprises a NIR fiber bundle coupled to the sensor head.

Clause 13. The apparatus of Clause 12, wherein a sensing region of the NIR spectroscopy device is less than 3 millimeters in diameter.

Clause 14. The apparatus of Clause 12, wherein a sensing region of the NIR spectroscopy device is between 2 and 5 millimeters in diameter.

Clause 15. The apparatus of Clause 12, wherein a sensing region of the NIR spectroscopy device is between 3 and 15 millimeters in diameter.

Clause 16. The apparatus of Clause 12, wherein a sensing region of the NIR spectroscopy device is between 10 and 25 millimeters in diameter.

Clause 17. The apparatus of Clause 12, wherein a sensing region of the NIR spectroscopy device is greater than 15 millimeters in diameter.

Clause 18. The apparatus of any of the previous clauses, wherein the plurality of non-invasive sensors comprises a pulse oximetry device, wherein the apparatus further comprises a fiber bundle.

Clause 19. The apparatus of Clause 18, wherein a sensing region of the pulse oximetry device is less than or equal to 3 millimeters in diameter.

Clause 20. The apparatus of Clause 18, wherein a sensing region of the pulse oximetry device is between 2 and 5 millimeters in diameter.

Clause 21. The apparatus of Clause 18, wherein a sensing region of the pulse oximetry device is between 3 and 15 millimeters in diameter.

Clause 22. The apparatus of Clause 18, wherein a sensing region of the pulse oximetry device is between 10 and 25 millimeters in diameter.

Clause 23. The apparatus of Clause 18, wherein a sensing region of the pulse oximetry device is greater than 15 millimeters in diameter.

Clause 24. The apparatus of any of the previous clauses, wherein the plurality of non-invasive sensors comprises a pulse oximetry device, wherein the apparatus further comprises a plurality of optical fibers.

Clause 25. The apparatus of Clause 18, wherein the plurality of optical fibers comprises an emitter having an emitter sensing region and a detector having a detector sensing region, wherein the emitter sensing region and the detector sensing region are spaced between 0.5 millimeters to 5 millimeters apart.

Clause 26. The apparatus of any of the previous clauses, wherein the plurality of non-invasive sensors comprises an OCT device, wherein the apparatus further comprises an optical fiber, an optical window and a mirror.

Clause 27. The apparatus of any of the previous clauses, wherein a processor is in communication with each of the plurality of noninvasive sensors, wherein the processor is configured to:
receive the physiological data from each of the plurality of noninvasive sensors; and
determine a physiological parameter based at least in part on the physiological data.

Clause 28. The apparatus of Clause 27, wherein the physiological parameter comprises a concentration of blood glucose.

Clause 29. The apparatus of any of the previous clauses, wherein each of the plurality non-invasive physiological sensors interrogate an overlapping portion of tissue.

Clause 30. The apparatus of any of the previous clauses, wherein each of the plurality non-invasive physiological sensors interrogate a portion of tissue within an area defined by the perimeter of the surface of the sensor head.

Clause 31. The apparatus of any of the previous clauses, wherein each of the plurality of noninvasive sensors obtain the physiological data from an identical tissue site.

Clause 32. The apparatus of any of the previous clauses, wherein each of the plurality of noninvasive sensors obtain the physiological data from a same tissue site.

Clause 33. The apparatus of Clause 32, wherein the same tissue site is a region less than 15 millimeters in diameter.

Clause 34. The apparatus of any of Clauses 32 or 33, wherein the same tissue site is a region between 8 millimeters and 13 millimeters in diameter.

Clause 35. The apparatus of Clause 32, wherein the same tissue site comprises a region greater than 15 millimeters in diameter.

Clause 36. The apparatus of any of the previous clauses, wherein each of the plurality of noninvasive sensors obtain the physiological data from proximate tissue sites.

Clause 37. The apparatus of any of the previous clauses, wherein proximate tissue sites comprises tissue sites within 5 millimeters of each other.

Clause 38. The apparatus of any of Clauses 32 or 33, wherein each of the plurality of noninvasive sensors obtain the physiological data from at least partially overlapping tissue sites.

Various example features can be found in the following clauses, which can be implemented together with any combination of the features described above:

Clause 1. A method comprising:
  receiving a first data signal from a first noninvasive sensor, wherein the first data signal is associated with first physiological data obtained from a first tissue region of a patient by the first noninvasive sensor;
  receiving a second data signal from a second noninvasive sensor, wherein the second data signal is associated with second physiological data obtained from a second tissue region of a patient by the second noninvasive sensor, wherein the first and second tissue regions are at least proximate to each other; and
  determining a physiological parameter based at least in part on the first and second data signals.

Clause 2. The method of Clause 1, wherein the first and second noninvasive sensors are oriented and/or positioned on or within a frame of a sensor head.

Clause 3. The method of any of the previous clauses, wherein the sensor head comprises:
  a surface configured to contact a third region tissue of the patient, and a frame configured to support at least a portion of each of the first and second noninvasive sensors, wherein the third region of tissue comprises at least a portion of the first and second regions of tissue.

Clause 4. The method of Clause 3, wherein the surface of the sensor head is between 5 and 15 millimeters in diameter.

Clause 5. The method of any of Clauses 3 or 4, wherein the surface of the sensor head is less than 15 millimeters in diameter.

Clause 6. The method of any of Clauses 3 to 5, wherein the surface of the sensor head is less than 30 millimeters in diameter.

Clause 7. The method of any of the previous clauses, further comprising.
  receiving a third data signal from a third noninvasive sensor, wherein the third data signal is associated with third physiological data obtained from a third tissue region of a patient by the third noninvasive sensor, wherein the first, second, and third tissue regions are at least proximate to each other.

Clause 8. The method of any of the previous clauses, wherein the first and second noninvasive sensors are configured to simultaneously obtain the first and second physiological data.

Clause 9. The method of any of the previous clauses, the first and second noninvasive sensors are configured to obtain the physiological data at non-overlapping time intervals.

Clause 10. The method of any of the previous clauses, wherein the first non-invasive sensor comprises at least one of an optical coherence tomography (OCT) device, a Raman spectroscopy device, a bio-impedance-sensing device, a temperature-sensing device, a NIR spectrometer device or a pulse oximetry device, wherein the second non-invasive sensor comprises a different one of the optical coherence tomography (OCT) device, the Raman spectroscopy device, the bio-impedance-sensing device, the temperature-sensing device, the NIR spectrometer device or the pulse oximetry device.

Clause 11. The method of any of the previous clauses, wherein the first non-invasive sensor comprises a Raman spectroscopy device, wherein the Raman spectroscopy device comprises a Raman lens tube coupled to the sensor head.

Clause 12. The method of Clause 11, wherein a sensing region of the Raman spectroscopy device is less than 3 millimeters in diameter.

Clause 13. The method of Clause 11, wherein a sensing region of the Raman spectroscopy device is between 2 and 5 millimeters in diameter.

Clause 14. The method of Clause 11, wherein a sensing region of the Raman spectroscopy device is between 3 and 15 millimeters in diameter.

Clause 15. The method of Clause 11, wherein a sensing region of the Raman spectroscopy device is between 10 and 25 millimeters in diameter.

Clause 16. The method of Clause 11, wherein a sensing region of the Raman spectroscopy device is greater than 15 millimeters in diameter.

Clause 17. The method of any of the previous clauses, wherein the first non-invasive sensor comprises a pulse oximetry device, wherein the pulse oximetry device comprises a fiber bundle.

Clause 18. The method of Clause 17, wherein a sensing region of the pulse oximetry device is less than or equal to 3 millimeters in diameter.

Clause 19. The method of Clause 17, wherein a sensing region of the pulse oximetry device is between 2 and 5 millimeters in diameter.

Clause 20. The method of Clause 17, wherein a sensing region of the pulse oximetry device is between 3 and 15 millimeters in diameter.

Clause 21. The method of Clause 17, wherein a sensing region of the pulse oximetry device is between 10 and 25 millimeters in diameter.

Clause 22. The method of Clause 17, wherein a sensing region of the pulse oximetry device is greater than 15 millimeters in diameter.

Clause 23. The method of any of the previous clauses, wherein the first non-invasive sensor comprises a pulse oximetry device, wherein the pulse oximetry device comprises a plurality of optical fibers.

Clause 24. The method of Clause 23, wherein the plurality of optical fibers comprises an emitter having an emitter sensing region and a detector having a detector sensing region.

Clause 25. The method of Clause 24, wherein the emitter sensing region and the detector sensing region are spaced 3 millimeters apart.

Clause 26. The method of Clause 24, wherein the emitter sensing region and the detector sensing region are spaced between 1.5 millimeters and 5 millimeters apart.

Clause 27. The method of any of the previous clauses, wherein the first non-invasive sensor comprises an OCT device, wherein the OCT device comprises an optical fiber and a mirror.

Clause 28. The method of any of the previous clauses, wherein the physiological parameter comprises a concentration of blood glucose.

Clause 29. The method of any of the previous clauses, the first and second regions of tissue are at least partially overlapping regions of tissue.

Clause 30. The method of any of the previous clauses, the first and second regions of tissue are within an area defined by a perimeter of the surface of the sensor head.

Clause 31. The method of any of the previous clauses, the first and second regions of tissue are identical tissue regions.

Clause 32. The method of any of the previous clauses, the first and second regions of tissue are a same tissue region.

Clause 33. The method of Clause 32, wherein the same tissue region is an area less than 15 millimeters in diameter.

Clause 34. The method of Clause 32, wherein the same tissue region is an area between 8 millimeters and 13 millimeters in diameter.

Clause 35. The method of Clause 32, wherein the same tissue region is an area greater than 15 millimeters in diameter.

Clause 36. The method of any of the previous clauses, wherein proximate tissue sites comprise tissue sites within 5 millimeters of each other.

TERMINOLOGY

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figures. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A multi-sensor apparatus measuring physiological parameters from a tissue site of a patient, the apparatus comprising:
  a plurality of non-invasive sensors configured to obtain physiological data from an overlapping area of the tissue site of a patient; and
  a sensor head comprising:
    a frame comprising a plurality of angled cavities, each of the plurality of angled cavities fixedly orienting one of the plurality of non-invasive sensors relative to the frame, each of the plurality of non-invasive sensors configured to emit light along a light path towards the overlapping area of the tissue site, wherein at least one of the plurality of cavities is non-parallel to another one of the plurality of cavities such that, when the multi-sensor apparatus is in use, the light paths of each of the plurality of non-invasive sensors converge on the overlapping area of the tissue site; and
    a tissue interaction section configured to be proximate the tissue site of the patient, wherein each of the plurality of non-invasive sensors are configured to obtain the physiological data associated with the patient at the tissue site.

2. The apparatus of claim 1, wherein the tissue interaction section comprises a different sensing region for each of the plurality of non-invasive sensors, wherein a particular non-invasive sensor obtains the physiological data via a particular sensing region.

3. The apparatus of claim 2, wherein a distance between each of the sensing regions satisfies a distance threshold.

4. The apparatus of claim 1, wherein at least two of the plurality of non-invasive sensors are configured to simultaneously obtain the physiological data.

5. The apparatus of claim 1, wherein at least two of the plurality of non-invasive sensors are configured to obtain the physiological data at non-overlapping time intervals.

6. The apparatus of claim 1, wherein each of the plurality of non-invasive sensors obtains the physiological data from the tissue site.

7. The apparatus of claim 1, wherein the plurality of non-invasive sensors obtain the physiological data from a plurality of regions of the tissue site, wherein each of the plurality of regions of the tissue site is proximate to one of the plurality of regions of the tissue site.

8. The apparatus of claim 1, wherein the plurality of non-invasive sensors comprises at least two of an optical coherence tomography (OCT) device, a Raman spectroscopy device, a bio-impedance-sensing device, a temperature-sensing device, or a pulse oximetry device.

9. The apparatus of claim 1, wherein the plurality of non-invasive sensors comprises an OCT device, a Raman spectroscopy device, a bio-impedance-sensing device, a temperature-sensing device, and a pulse oximetry device.

10. The apparatus of claim 1, wherein the plurality of non-invasive sensors comprises a Raman spectroscopy device, wherein the apparatus further comprises a Raman lens tube coupled to the sensor head.

11. The apparatus of claim 1, wherein the tissue interaction section is configured to contact the tissue site of the patient.

12. The apparatus of claim 1, further comprising a processor configured to:
  receive the physiological data from each of the plurality of non-invasive sensors; and
  determine a physiological parameter based at least in part on the physiological data.

13. A system for measuring physiological parameters from a tissue site of a patient, the system comprising:
  a multi-sensor apparatus, the multi-sensor apparatus comprising:
    a plurality of non-invasive sensors configured to obtain physiological data from an overlapping area of the tissue site of a patient; and
    a sensor head comprising:
      a frame comprising a plurality of angled cavities, each of the plurality of angled cavities fixedly orienting one of the plurality of non-invasive sensors relative to the frame, each of the plurality of non-invasive sensors configured to emit light along a light path towards the overlapping area of the tissue site, wherein at least one of the plurality of cavities is non-parallel to another one of the plurality of cavities such that, when the multi-sensor apparatus is in use, light paths of each of the plurality of non-invasive sensors converge on the overlapping area of the tissue site, and
      a tissue interaction section configured to be proximate the tissue site of the patient, wherein each of the plurality of non-invasive sensors are configured to obtain the physiological data from the tissue site; and one or more processors in communication with the multi-sensor apparatus, the one or more processors configured to:
  receive the physiological data from each of the plurality of non-invasive sensors; and
  determine a physiological parameter based at least in part on the physiological data.

14. The system of claim 13, wherein the tissue interaction section comprises a plurality of sensing regions, wherein each of the plurality of sensing regions corresponds to one or more of the plurality of non-invasive sensors, wherein a particular non-invasive sensor obtains the physiological data via a particular sensing region.

15. The system of claim 13, wherein at least two of the plurality of non-invasive sensors are configured to simultaneously obtain the physiological data.

16. The system of claim 13, wherein at least two of the plurality of non-invasive sensors are configured to obtain the physiological data at non-overlapping time intervals.

17. The system of claim 13, wherein the plurality of non-invasive sensors comprises at least two of an optical coherence tomography (OCT) device, a Raman spectroscopy device, a bio-impedance-sensing device, a temperature-sensing device, or a pulse oximetry device.

18. The system of claim 13, wherein the plurality of non-invasive sensors comprises an OCT device, a Raman spectroscopy device, a bio-impedance-sensing device, a temperature-sensing device, and a pulse oximetry device.

19. The system of claim 13, wherein the tissue interaction section comprises a lower surface, the lower surface having a diameter or width of between 5 mm and 30 mm.

20. The apparatus of claim 1, wherein the tissue interaction section comprises a lower surface, the lower surface having a diameter or width of between 5 mm and 30 mm.

* * * * *